US008187572B2

(12) United States Patent
Benardeau et al.

(10) Patent No.: US 8,187,572 B2
(45) Date of Patent: May 29, 2012

(54) DIABETOGENIC RAT MODEL

(75) Inventors: Agnes Benardeau, St. Louis (FR); Emmanuelle Hainaut, Allschwil (CH); Philippe Verry, Lutter (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 1177 days.

(21) Appl. No.: 11/481,080

(22) Filed: Jul. 5, 2006

(65) Prior Publication Data

US 2007/0009439 A1    Jan. 11, 2007

(30) Foreign Application Priority Data

Jul. 8, 2005    (EP) .................................... 05106244

(51) Int. Cl.
*A61K 49/00* (2006.01)
*A01K 67/00* (2006.01)
*A01K 67/033* (2006.01)
*A01K 67/027* (2006.01)

(52) U.S. Cl. ................. 424/9.2; 514/866; 800/9; 800/14

(58) Field of Classification Search ................... 424/9.2; 514/866; 800/9, 14
See application file for complete search history.

(56) References Cited

FOREIGN PATENT DOCUMENTS
JP        2003052312        2/2003

OTHER PUBLICATIONS

Corsetti (Atherosclerosis, 148 (2000) 231-241).*
Sudre et al (Diabetes, vol. 51, (2002) 1461-1469).*
Anders et al (Animal Models of Diabetes: A Primer, Harwood Academic Publishers, Amsterdam, 2001).*
Shibata et al., *British Journal of Pharmacology* 130, 495-504 (2000).
Boden, G. (2003). Effects of free fatty acids on gluconeogenesis and glycogenolysis. *Life sciences*, 72, 977-88.
Brand, C., L., et al., (2003). *American journal of physiology. Endocrinology and metabolism*. pp. E841-E854. United-States.: NLM.
Chen, D. et al. (2004). Development and applications of rodent models for type 2 diabetes. *Diabetes, Obesity and Metabolism*, 7, 307-317.
Goldstein, B.J. (2002). Insulin resistance as the core defect in type 2 diabetes mellitus. *American Journal of Cardiology*, 90, 3G-10G.
Greenfield, J., R. & Campbell, L., V. (2004). Insulin resistance and obesity. *Clinics in dermatology*, 22, 289-95.
Griffin, M.E., et al., (1999). Free fatty acid-induced insulin resistance is associated with activation of protein kinase C theta and alterations in the insulin signaling cascade. *Diabetes*, 48, 1270-4.
Grundy, S., M., et al., (2004). Definition of metabolic syndrome: Report of the National Heart, Lung, and Blood Institute/American Heart Association conference on scientific issues related to definition. *Circulation*, 109, 433-8.
Gurnell, M., et al., (2003). The metabolic syndrome: peroxisome proliferator-activated receptor gamma and its therapeutic modulation. *The Journal of clinical endocrinology and metabolism*, 88, 2412-21.
Kahn, B.B. (1998). Type 2 diabetes: when insulin secretion fails to compensate for insulin resistance. *Cell*, 92,593-596.

(Continued)

*Primary Examiner* — Benjamin Packard
(74) *Attorney, Agent, or Firm* — George W. Johnston; Dennis P. Tramaloni; Brian C. Remy

(57) ABSTRACT

The present invention provides a method of producing diabetic rats, and a method for identifying compounds that reverse diabetes in said rats.

4 Claims, 12 Drawing Sheets

OTHER PUBLICATIONS

King, H., Aubert, R.E. & Herman, W.H. (1998). Global burden of diabetes, 1995-2025: prevalence, numerical estimates, and projections. *Diabetes care*, 21, 1414-31.

Klein, R. (1995). Hyperglycemia and microvascular and macrovascular disease in diabetes. *Diabetes care*, 18, 258-68.

Randle, P.J., Garland, P.B., Hales, C.N. & Newsholme, E.A. (1963). The glucose fatty-acid cycle its role in insulin sensitivity and the metabolic disturbances of diabetes mellitus. *Lancet*, 1, 785-9.

Matsuzawa, Y., Funahashi, T. & Nakamura, T. (1999). Molecular mechanism of metabolic syndrome X: contribution of adipocytokines adipocyte-derived bioactive substances. *Annals of the New York Academy of Sciences*, 892, 146-54.

Pickavance, L., et al., (2005). The dual PPARalpha/gamma agonist, ragaglitazar, improves insulin sensitivity and metabolic profile equally with pioglitazone in diabetic and dietary obese ZDF rats. *British journal of pharmacology*, 144, 308-16.

Pospisilik, J., et al., (2002a). *Diabetes*, 51, 2677-83.

Pospisilik, J.A., et al., (2002b). Long-term treatment with the dipeptidyl peptidase IV inhibitor P32/98 causes sustained improvements in glucose tolerance, insulin sensitivity, hyperinsulinemia, and beta-cell glucose responsiveness in VDF fa/fa Zucker rats. *Diabetes*, 51, 943-50.

Reaven, G.M. (1988). Banting lecture 1988 Role of insulin resistance in human disease. *Diabetes*, 37, 1595-607.

Rubin, R.J., et al. (1994). Health care expenditures for people with diabetes mellitus, 1992. *The Journal of clinical endocrinology and metabolism*, 78, 809A-809F.

Scherrer, U. & Sartori, C. (1997). Insulin as a vascular and sympathoexcitatory hormone: implications for blood pressure regulation, insulin sensitivity, and cardiovascular morbidity. *Circulation*, 96, 4104-13.

Schneider, S.H. & Morgado, A. (1995). Effects of fitness and physical training on carbohydrate metabolism and associated cardiovascular risk factors in patients with diabetes. *Diabetes Reviews*, 3, 378-407.

Stiegler, H., et al. (1992). Morbidity, mortality, and albuminuria in type 2 diabetic patients: a three-year prospective study of a random cohort in general practice. *Diabetic medicine*, 9, 646-53.

Teutsch, S., Newman, J. & Eggers, P. (1989). The problem of diabetic renal failure in the United States: an overview. *American journal of kidney diseases*, 13, 11-3.

Tinker, L.F., Heins, J.M. & Holler, H.J. (1994). Commentary and translation: 1994 nutrition recommendations for diabetes Diabetes Care and Education, a Practice Group of the American Dietetic Association. *Journal of the American Dietetic Association*, 94, 507-11.

UKPDS. (1998). Intensive blood-glucose control with sulphonylureas or insulin compared with conventional treatment and risk of complications in patients with type 2 diabetes UKPDS 33 UK Prospective Diabetes Study UKPDS Group. *Lancet*, 352, 837-53.

Corsetti, JP, et al., Atherosclerosis, vol. 148, No. 2, pp. 231-241 (2000), XP002464301.

Desu Chen, et al., Diabetes Obesity and Metabolism, vol. 7, No. 4, pp. 307-317 (2005), XP002464302.

Charles River Laboratories, Research Models: Informational Rsources: ZDF Rat, Internet Article (2003), XP002464308.

Verry Philippe, et al., Diabetes, vol. 54, No. Supl, p. A659 (2005), XP008087098.

Rees DA, et al., Diabet Med., vol. 22, No. 4, pp. 359-370 (2005), XP002464303.

Srinivasan, K., et al., Indian J. Med. Res., vol. 125, No. 3, pp. 451-472 (2007), XP002464304.

Pickavance, L.C., et al., British Journal of Pharmacology, vol. 128, No. 7, pp. 1570-1576 (1999), XP002456451.

Pickavance, L., et al., British Journal of Pharmacology, vol. 125, pp. 767-700 (1998), XP002464305.

Dryden, et al., Brain Research, vol. 690, No. 2, pp. 185-188 (1995), XP022257269.

Alemzadeh, R., et al., Endocrinology, vol. 145, No. 12, pp. 5476-484 (2004), XP002464307.

Kliba Nafag, Mice/Rats Maintenance feed + Experimental Diets, Internet Article (2008), XP002464626.

Teague et al., "Reversibility of hyperglycaemia and islet abnormalities in the high fat-fed female ZDF rat model of the type 2 diabetes" *Journal of Pharmacological and Toxicological Methods* 63:15-23 (2011).

Etgen et al., "Profiling of Zucker Diabetic Fatty Rats in Their Progression to the Overt Diabetic State" *Metabolism* 49(5):684-688 (May 2000).

\* cited by examiner

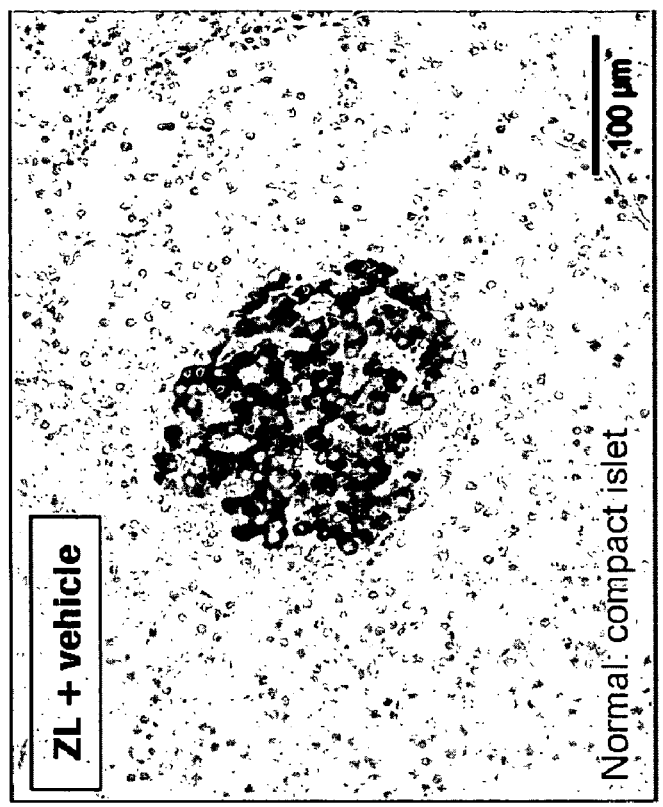
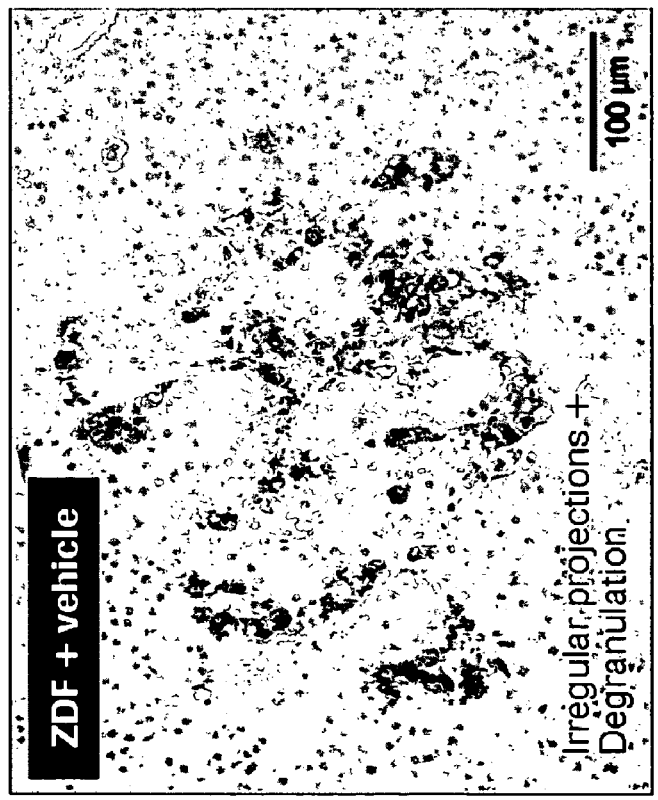
Figure 7

DIABETOGENIC RAT MODEL

PRIORITY TO RELATED APPLICATIONS

This application claims the benefit of European Application No. 05106244.6, filed Jul. 8, 2005, which is hereby incorporated by reference in its entirety.

BACKGROUND OF THE INVENTION

The past decades have witnessed a dramatic increase in the prevalence of obesity and type-2-diabetes (T2D) primarily in US but also progressing in Europe and in developing countries. All over the world, T2D represents 85-90% of all the cases of diabetes (inherited insulin-dependent diabetes or T1D and non-insulin-dependent-diabetes Mellitus or T2D) (King et al., 1998). Although several mutations affecting leptin pathway, insulin secretion or its receptor, or GLUT4 (glucose transport sensitive to insulin) have been identified, most of the cases of obesity and T2D are from non-genetic origin and triggered by life style (reduction of physical activity, highly calorie diets, etc). T2D and obesity are both associated with high morbidity, mortality (Stiegler et al., 1992), and health care costs (Rubin et al., 1994).

The primary feature of T2D is insulin resistance and defect in insulin secretion. Insulin is a key hormone synthesized and secreted by pancreatic beta-cells, that stimulates glucose uptake in various organs (particularly muscle, liver, and adipose tissue). Insulin also regulates Hepatic Glucose Production (HGP) via controlling the expression of the gene encoding glucose-6-phosphatase and inhibits lipolysis in adipose tissue (Murray et al., 2000). Impaired insulin action (i.e. insulin resistance) occurs when target tissues are unable to respond to normal concentrations of insulin.

Once this deregulation starts and in absence of treatment, beta-cells secrete increased amount of insulin (=hyperinsulinemia) to maintain euglycemia (normal circulating glucose levels). However, in the absence of treatment, beta-cells fail producing enough insulin, leading to increase in circulating glucose (hyperglycaemia) (FIG. 1). As long as enough beta-cells will be viable and will be secreting the appropriate rate of insulin to maintain euglycemia, T2D does not arise (Kahn, 1998). The mechanisms leading to insulin resistance have been extensively explored during the past years by many groups. It is widely accepted that the accumulation of free fatty acids (FFA) in insulin-sensitive non adipose tissues (liver & muscles), can impair insulin-mediated-glucose uptake in these tissues. (Randle et al., 1963). Moreover, increased lipid production by the liver enhances fatty acid oxidation, decreases insulin-dependent inhibition of hepatic glucose production and, therefore, increases gluconeogenesis (GNG), further worsening the hyperglycaemia (Boden, 2003).

Development of T2D is associated with other metabolic disturbances. The cluster of insulin resistance, impaired glucose tolerance, arterial hypertension, abdominal obesity and dyslipidemia, called metabolic syndrome (Syndrome X) (Reaven, 1988), has been defined by the Adult Treatment Panel III (ATPIII) as a grouping of factors that underlie major cardiovascular risk (Grundy et al., 2004). Many preclinical studies suggested a predominant role of insulin in the development of hypertension in T2D patients (Scherrer et al., 1997). However, the primary focus of clinical care is to diagnose and treat the abnormalities in glucose metabolism. Indeed high blood glucose is a major risk factor for microvascular complications as reported by the UK Prospective Diabetes Study (UKPDS, 1998). It was shown that maintenance of glucose levels near to normal in T2D patients prevents the onset of defects such as neuropathy (occurring in 50% to 60% of T2D patients), retinopathy and nephropathy (diabetes are the leading causes of blindness and end-stage renal failure in the U.S) (Klein, 1995; Teutsch et al., 1989).

Some years ago, non-pharmacological therapy took place in the US, based on diet, exercise and weight loss (Tinker et al., 1994). These major lifestyle modifications did not only lower blood glucose concentration, but also reduced or delayed occurrence of risk factors for cardiovascular diseases (CVD) in overweight diabetic patients (Schneider et al., 1995). However, diabetic patients with advanced disease require specific medication to control their glycaemia and to substantially prevent or reduce appearance of complications. Current anti-diabetic therapy is based on a tight control of circulating glucose by either (1) improving insulin production by the use of agents commonly known as insulin secretagogues or (2) improving whole body insulin action with or without inhibition of hepatic glucose production by agents known as insulin sensitizers (FIG. 1).

The anti-diabetic drugs from the thiazolidinediones (TZDs) class (available in the US since 1997), currently represented by Rosiglitazone (Avandia®), Pioglitazone (Actos®), and Troglitazone (Rezulin®), are efficacious drugs in increasing peripheral insulin-mediated-glucose-uptake. TZDs are pharmacological agonists of peroxisome-proliferator-activated receptor (PPAR gamma), a transcription factor of the nuclear hormone receptor family that controls the expression of genes in glucose and lipid metabolism. PPAR gamma drugs reduced hyperglycaemia, hyperlipidemia and hyperinsulinemia and improved insulin sensitivity by increasing differentiation and proliferation of pre-adipocytes into mature fat cells, particularly in peripheral fat depots (Gurnell et al., 2003). Thus PPAR gamma activation increases fatty acids storage in peripheral adipocytes, lowers circulating fatty acids and reduces triglycerides levels in muscle and liver. PPAR gamma drugs alter the expression of several circulating factors such as adiponectin, TNF alpha and resistin, the levels of which are highly correlated to insulin resistance and the response to therapy (Greenfield et al., 2004).

Appropriate animal models of T2D and insulin resistance are essential preclinical tools for characterizing in vivo efficacy of therapeutic agents. Most of the animal models of T2D that have been developed in the past 20 years are genetic based. Spontaneously diabetic (or insulin resistant and obese) rodent models such as, db/db and ob/ob mice, GK, ZDF and fa/fa rats are most commonly used worldwide in drug discovery (Chen et al., 2004) (Table 1). Among these animal models, Zucker diabetic fatty (ZDF) rats when fed with diabetogenic diet (Purina 5008 or KLIBA 2437) represent the most attractive model since metabolic disorders (glucose intolerance, hyperglycaemia, insulin resistance and hypertriglyceridemia), beta-cell failure, obesity and mild hypertension develop similarly to humans, although in a more rapid progression. Early changes in main plasma parameters start at 7-8 weeks of age leading to overt diabetes (beta-cell and renal failure) at >=12 weeks of age (FIG. 2).

Due to this rapid metabolic deterioration, reversion of main feature of T2D in ZDF rats is not achieved by marketed anti-diabetics (Rosiglitazone (PPAR gamma) and Razaglitazar (PPAR alpha gamma)). Prevention of T2D was shown to be achieved, however, in ZDF rats under chronic treatment (13 weeks) (Shibata et al., 2000) or in very young and only moderately diabetic animals (Brand et al., 2003; Pickavance et al., 2005). It was reported by one team that in a slightly different T2D model called the VDF rat (Vancouver Diabetic Fatty), derived from Zucker and fa/fa strains, which was used by that interventional therapy with a DPPIV inhibitor was able to partially improve glucose tolerance, peripheral insulin sensitivity, and beta-cell function (Pospisilik et al., 2002a; Pospisilik et al., 2002b). It has to be noted that this model was not diabetic, being characterized by absence of hyperglycaemia, weak glucose intolerance and no peripheral insulin resistance. It was the aim of the present invention to develop a preclinical animal model that not only better represents the progression of type-2-diabetes in humans, but that also shows stronger responses to drug therapy.

FIG. 3: Study design

Scheme of the study design depicting different feeding periods performed in ZDF rats with diabetogenic diet (yellow bars) or chow diet (black straight lines). Lean ZDF (ZL) rats were fed a diabetogenic diet during the whole study duration. Treatment with Pioglitazone (indicated by red lines) started at the age of 10 weeks and was performed until age of 17 W. Each group was formed with 10 rats. A glucose tolerance test (OGTT) was performed at the end of the treatment period (after 6 weeks of treatment). Several blood samplings occurred before and during the treatment for biochemical analysis. Only 6 rats were considered for performing OGTT.

TABLE 1

Main pre-clinical rodent models of metabolic diseases.
Rodent models of metabolic diseases induced by diet or chemical agents.
B: Rodent models of insulin resistance and T2D induced by gene defects.

| A | Human | Diet induced | | | Chemically-induced STZ |
| --- | --- | --- | --- | --- | --- |
| | | DIO rats (SD) | DIO mice (AKR/J) | Sucrose fed rats | |
| Obesity origin | polygenic | polygenic | polygenic | polygenic | polygenic |
| T2D origin | polygenic | polygenic | polygenic | polygenic | polygenic |
| Leptin/Leptin R | normal | normal | normal | normal | normal |
| Degree of Obesity | Moderate | Severe | moderate | No | No |
| T2D onset | mature | mature | mature | mature | mature |
| Elevated TG | Yes | Moderate | Yes | Yes | Yes |
| Hyperglycaemia | Yes | No | Yes | ? | Yes |
| β-cell failure | variable | No/ | ? | ? | ? |
| Insulin resistance | Yes | Moderate | Yes | Yes | Yes |
| Hyperphagia | No | No | No | No | No |
| Hypercorticism | No | No | No | No | No |
| Liver steatosis | Variable | Variable | Variable | ? | ? |

| B | Human | Zucker fa/fa rats | ZDF rats | ob/ob mice | db/db mice |
| --- | --- | --- | --- | --- | --- |
| Obesity origin | polygenic | Monogenic: fa gene | Monogenic: fa gene | Monogenic | Monogenic |
| T2D origin | polygenic | No | polygenic | polygenic | polygenic |
| Leptin/Leptin R | normal | disrupted | disrupted | disrupted | disrupted |
| Degree of Obesity | Moderate | Severe | Severe | Severe | Severe |
| T2D onset | mature | No | mature | young | young |
| Elevated TG | Yes | Yes | Yes | Yes | Yes |
| Hyperglycaemia | Yes | No | Yes | Yes | Yes |
| β-cell failure | variable | No | variable | No | Yes |
| Insulin resistance | Yes | Yes | Yes | No | Yes |
| Hyperphagia | No | Yes | Yes | Yes | Yes |
| Hypercorticism | No | Yes | Yes | Yes | Yes |
| Liver steatosis | Variable | ? | ? | Yes | Yes |

SUMMARY OF THE INVENTION

The present invention relates to a method of producing a diabetic rat which can be used in a method of identifying compounds that can reverse diabetes and are suitable for interventive therapy in diabetes. The method comprises feeding a susceptible strain of rat a diabetogenic high fat content feed for 1-2 weeks followed by maintenance feeding with a lower fat content feed.

Scheme summarizing (1) inter-relation between glucose and lipid metabolism (2) factors and disturbance leading to insulin resistance and T2D. From: Prospects of research in Diabetes Mellitus (*JAMA*, 2001; 285:628-632).

Figure 1:
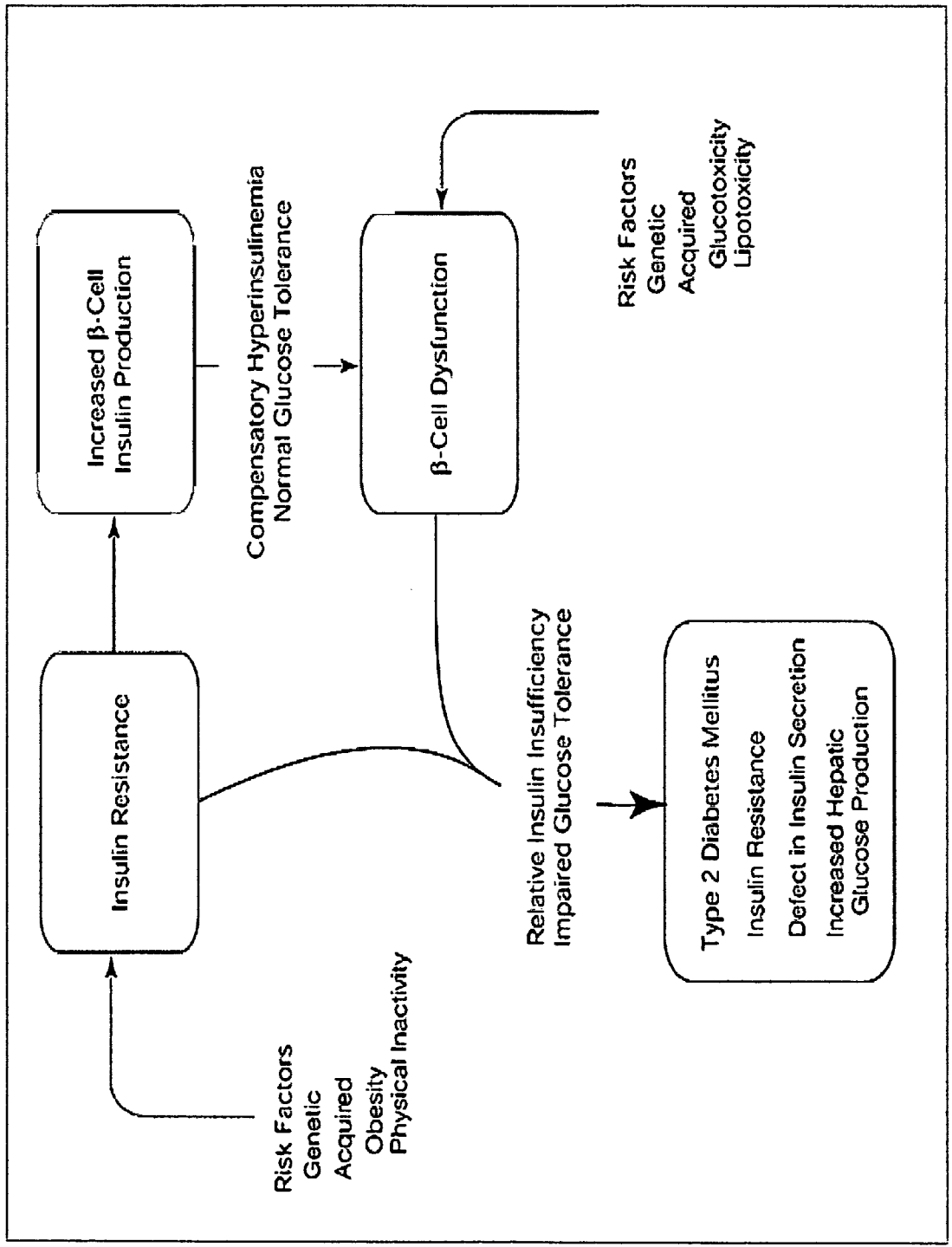
FIG. 1: Summary of metabolic defects: Implication of organs and pathways
Figure 2:
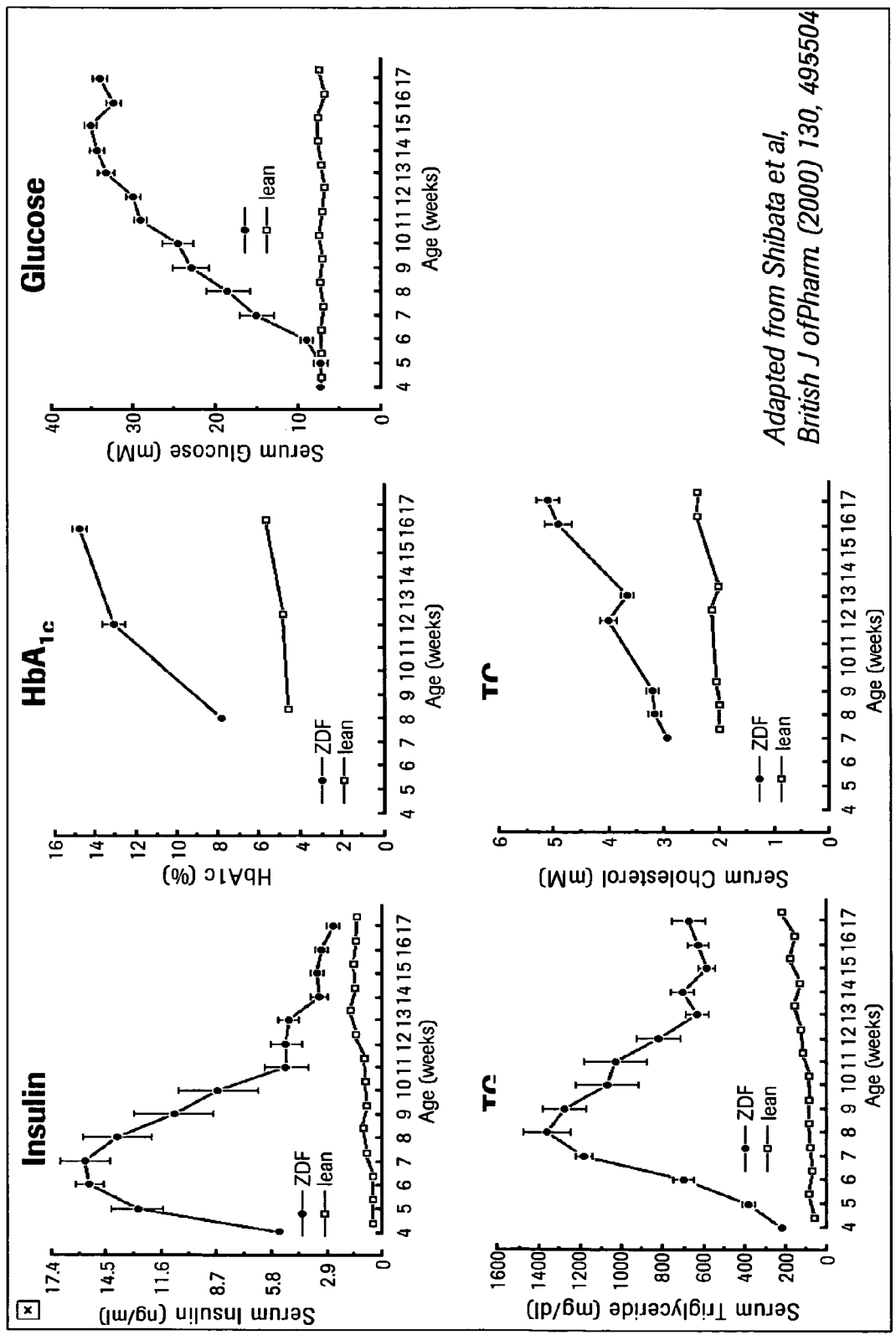

FIG. 2: Age-dependent changes in metabolic parameters in male ZDF rats

Adapted from Shibata et al., *British Journal of Pharmacology* 130, 495-504 (2000).

Figure 4:
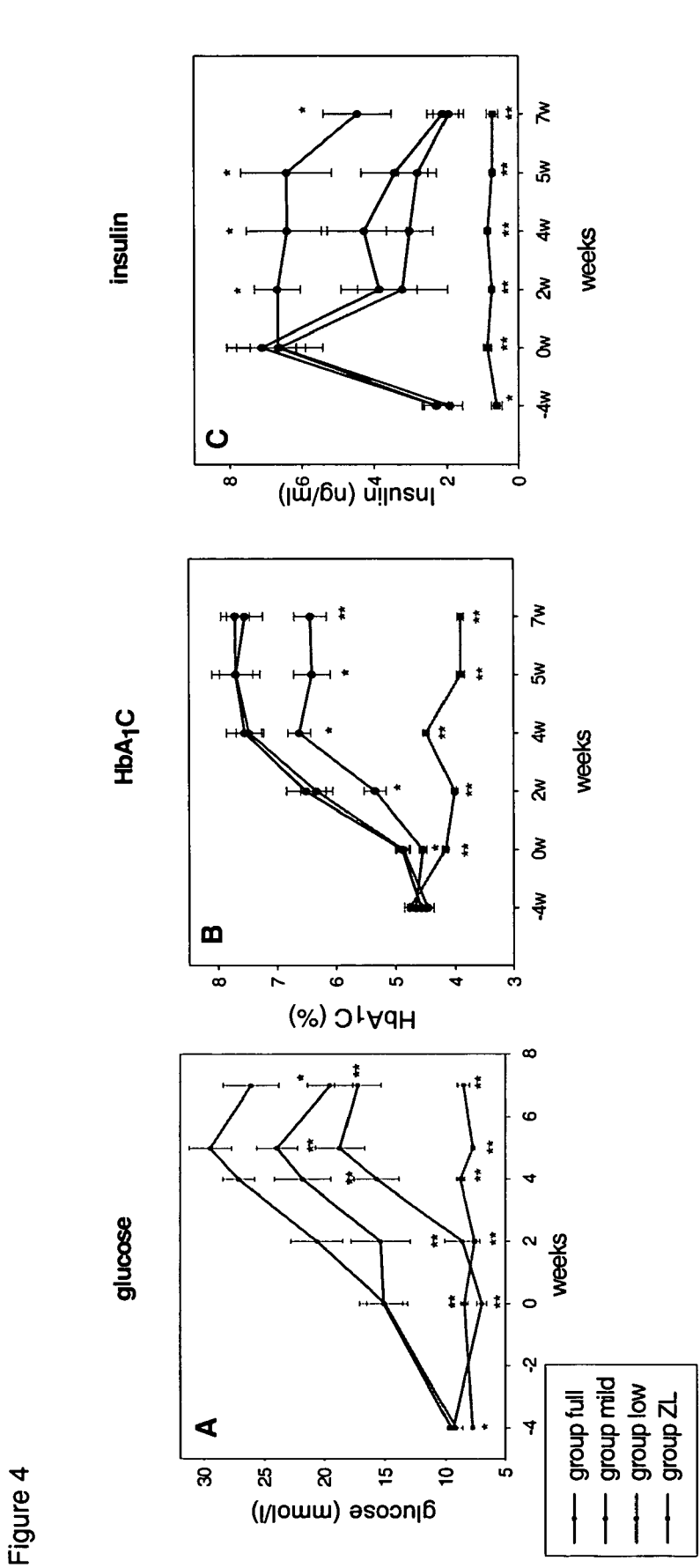

FIG. 4: Evolution of glucose, HbA1c and insulin levels in ZDF rats fed under diabetogenic or/and chow diet.

N=8-10 per group. Data are expressed as mean±SEM. ZDF and ZL were 6 w-old at baseline (treatment −4 weeks). *p<0.05 or **p<0.01 compared to group_full, ANOVA, followed by Dunnett's post hoc test. ZL compared to group_full by a Mann-Witney test.

Figure 5:
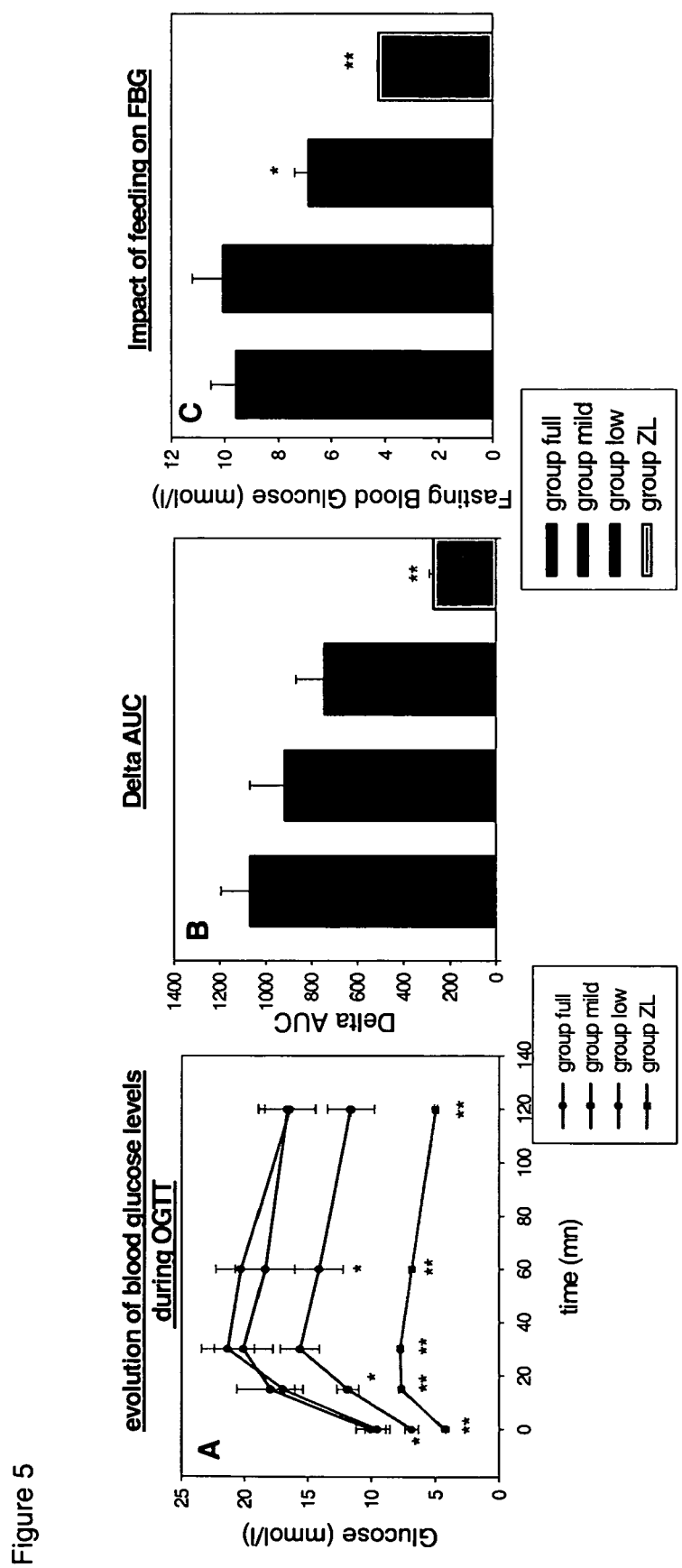

FIG. 5: Impact of diet on glucose tolerance of ZDF rats after 10 weeks of feeding.

N=8-10 per group. **p<0.01 or *p<0.05 compared to group_full. ANOVA followed by post hoc Dunnett's test. ZL compared to group_full by Mann-Whithney or t-test.

Figure 6:
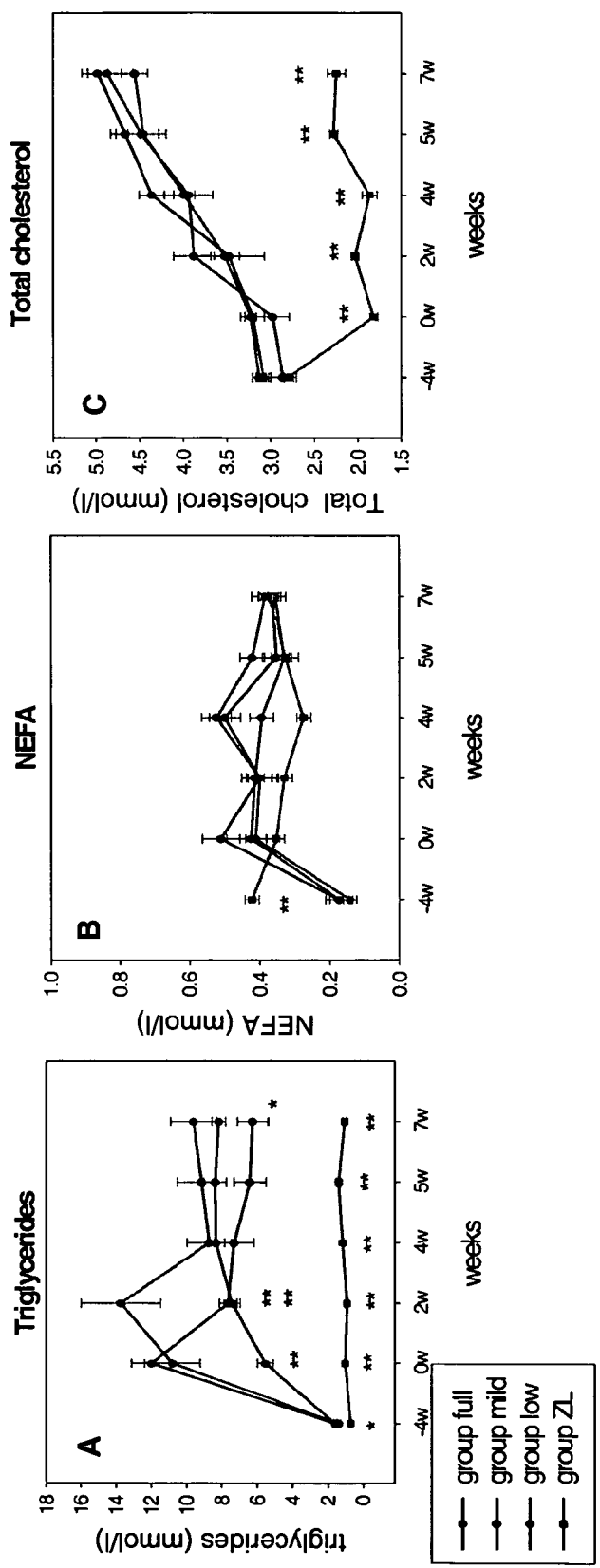

FIG. 6: Evolution of plasma TG, NEFA and TC levels in ZDF rats fed with diabetogenic or/and chow diet.

N=8-10 per group. Data are expressed as mean±SEM. ZDF and ZL were 6 w-old at baseline (treatment −4 weeks). *p<0.05 or **p<0.01 compared to group_full, ANOVA, followed by Dunnett's post hoc test.

FIG. 7: Immunohistochemistry of beta-cells in ZDF rats versus ZL rats.

Insulin was stained using antibody against insulin (immuno histochemistry method). Representative photographs are shown (among n=6 per group)

Figure 8:
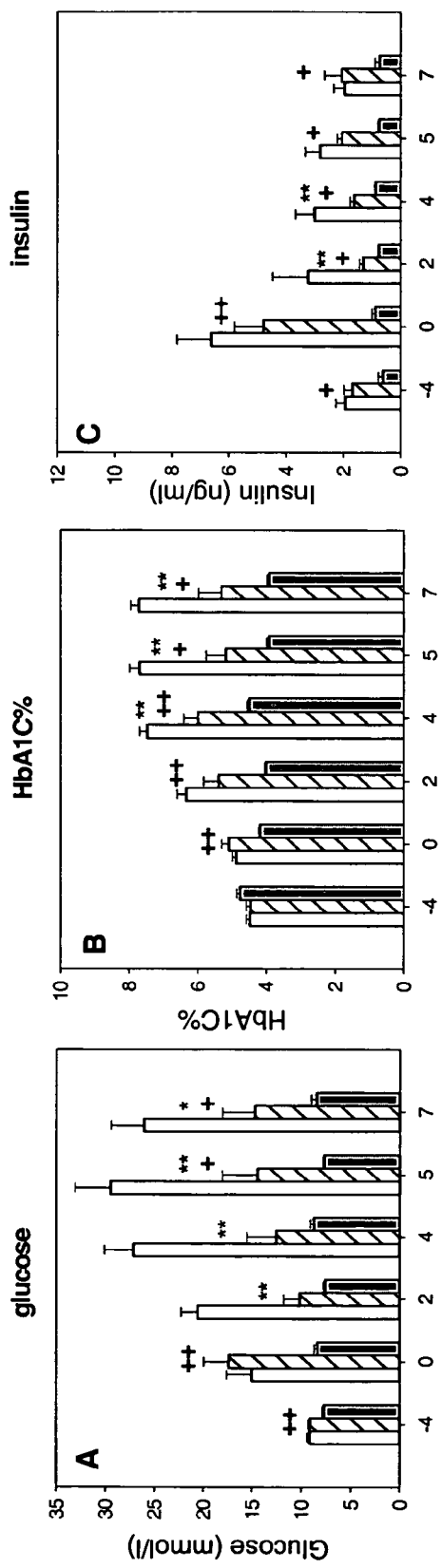
Figure 8:
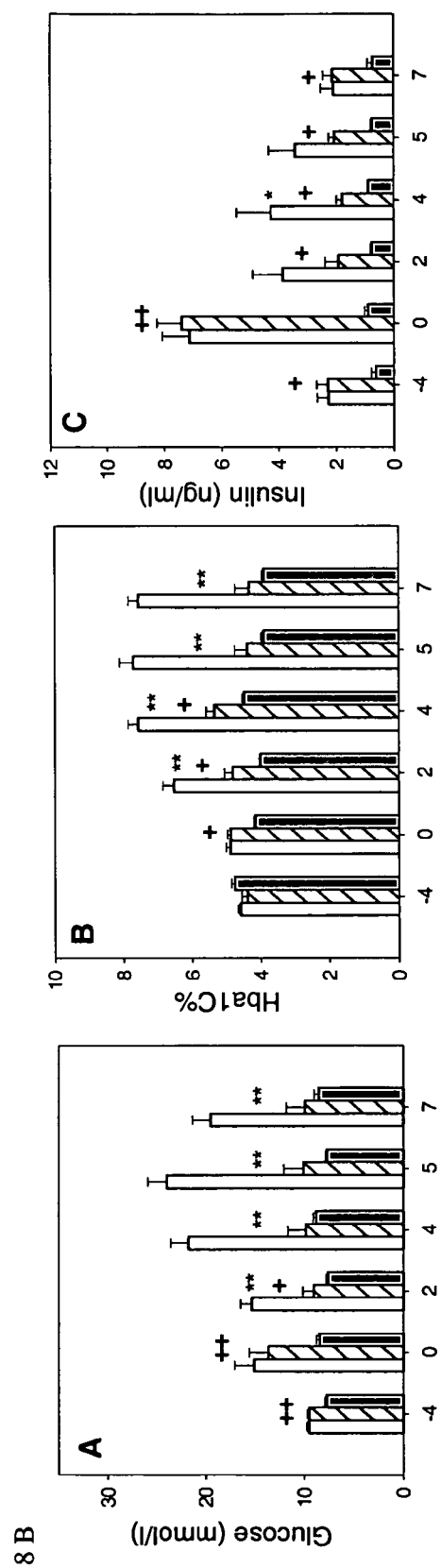
Figure 8:
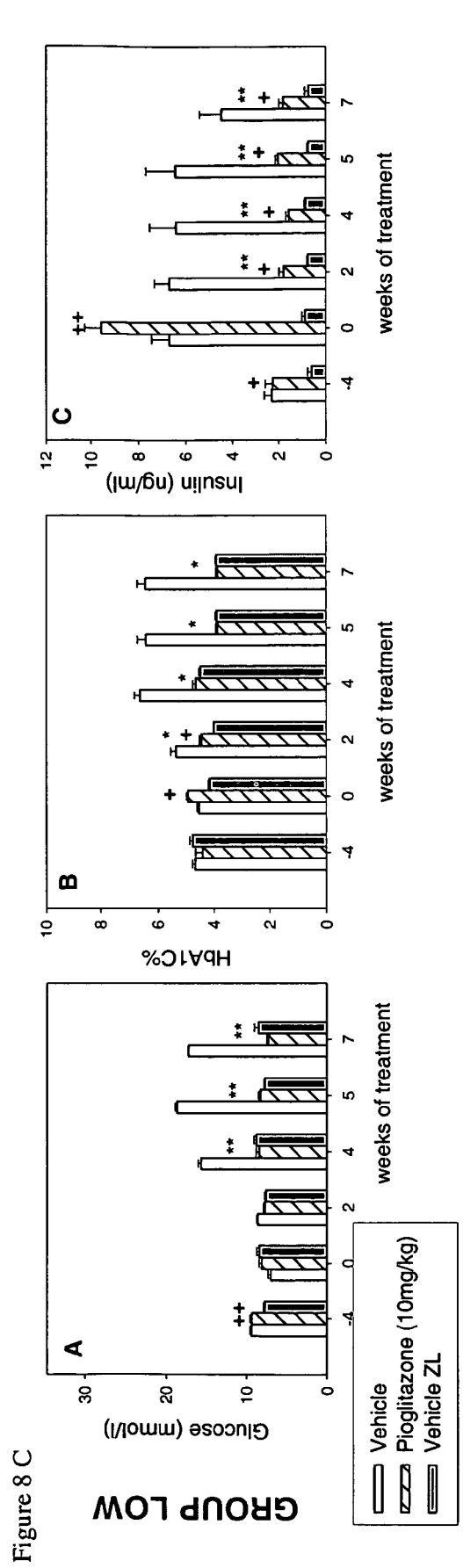

FIG. 8: Effects of Pioglitazone (10 mg/kg) glucose parameters (glucose [A], $HbA_{1C}$ [B] and insulin [C]) in different diet groups (group_full, group_mild and group_low).

Treatment started at 10 weeks of age and was administered as food-admix. Age-matched vehicle non treated ZDF and lean (ZL) rats were used as controls. Values are expressed as mean+SEM. N=8-10 per group. **$p<0.01$ or *$p<0.05$ compared to respective vehicle treated ZDF rats. ++$p<0.01$ or +$p<0.05$ compared to ZL rats. F-Test followed by TTest.

Figure 9:
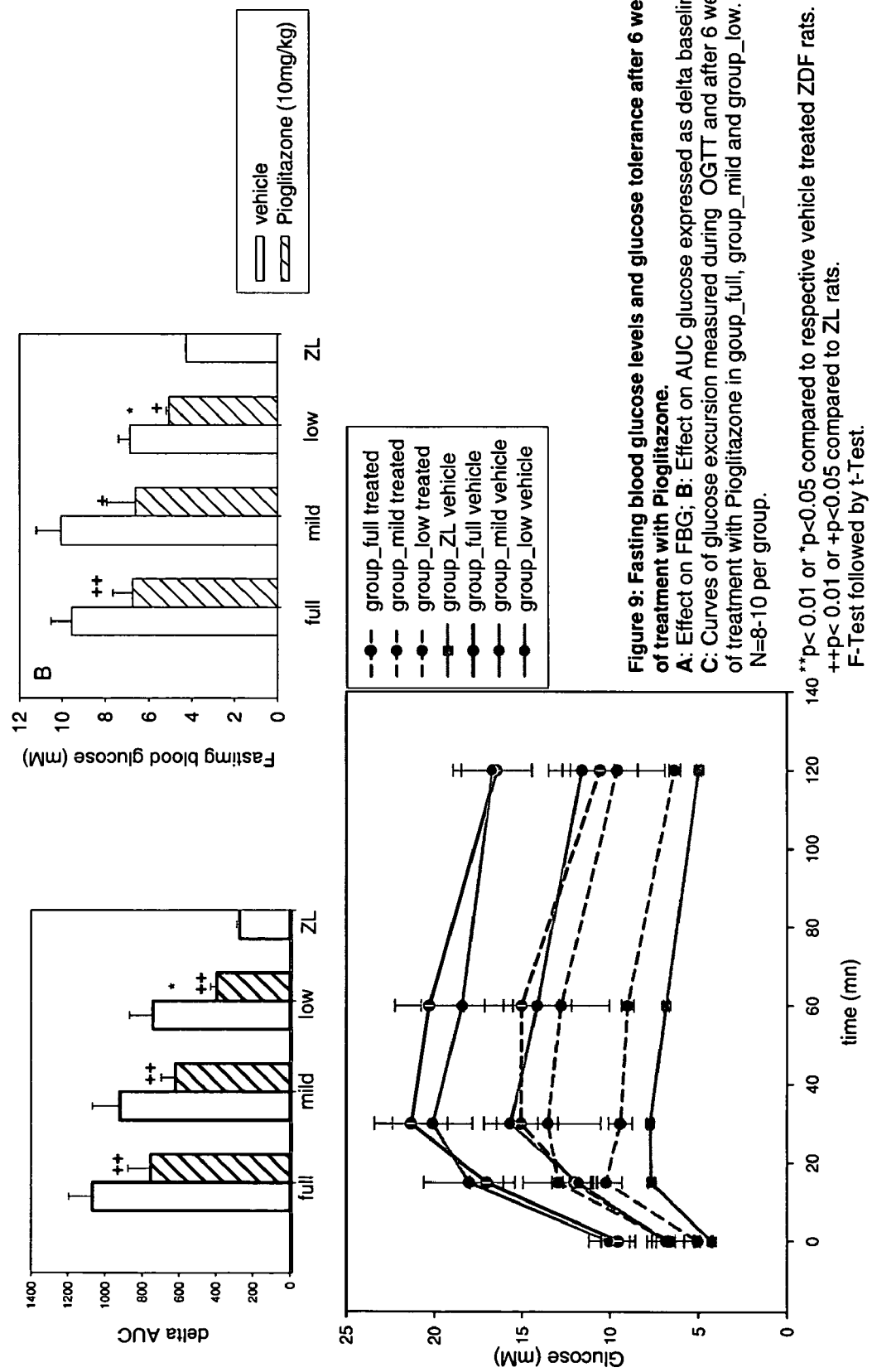

FIG. 9: Fasting blood glucose levels and glucose tolerance after 6 weeks of treatment with Pioglitazone.

A: Effect on FBG; B: Effect on AUC glucose expressed as delta baseline; C: Curves of glucose excursion measuring during OGTT and after 6 weeks of treatment with Pioglitazone in group_full, group_mild and group_low. N=8-10 per group.
**$p<0.05$ compared to respective vehicle treated ZDF rats. ++$p<0.01$ pr+$p<0.05$ compared to ZL rats.
F-Test followed by t-Test.

Figure 10:
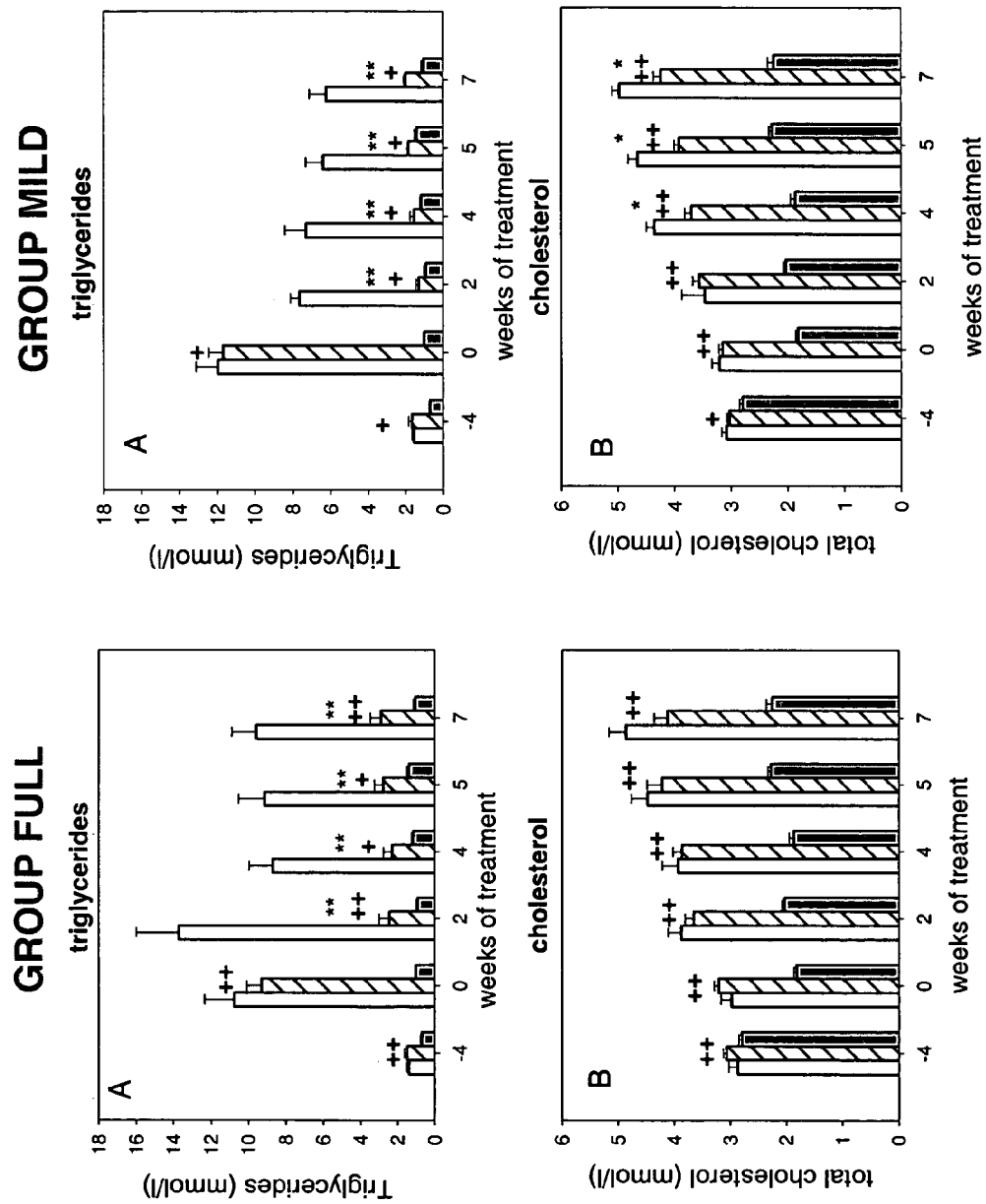

FIG. 10: Effects of Pioglitazone (10 mg/kg) on ZDF lipid parameters (triglycerides [A], Cholesterol [B]) in different diet groups (group_full, group_mild and group_low)

Treatment started at 10 weeks of age and was administered as food-admix. Age-matched vehicle non treated ZDF and lean (ZL) rats were used as controls. Values are expressed as mean+SEM. N=8-10 per group. **$p<0.01$ or *$p<0.05$ compared to respective vehicle treated ZDF rats. ++$p<0.01$ or +$p<0.05$ compared to ZL rats. F-Test followed by TTest.

DETAILED DESCRIPTION OF THE INVENTION

The present invention provides a diabetogenic method for raising rats that are less diabetic (closer to human situation) than normally achieved under diabetogenic diets with high fat content feeds such as LabDiet Formulab 5008 (Purina Mills, Inc.), and KLIBA 2437 (Provimi-Kliba, SA) containing at least 6.5% fat, in order to increase their sensitivity to intervention therapy with anti-diabetics as would be the case for humans. Rats strains capable of being so raised are preferably ZDF rats.

For this purpose, three groups of ZDF rats were fed with different diets. The first group received a diabetogenic diet (Kliba 2437) starting at weaning and for 11 consecutive weeks (group_full); a second group was fed a diabetogenic food for 4 weeks, followed by a chow diet (Kliba 3436, containing 4.5% fat, 18.5% protein) for 7 weeks (group_mild); a third group was fed a diabetogenic food for 2 weeks, then a chow diet for 9 weeks (group_low).

A diabetogenic diet is a diet which will render a strain (mice or rats) diabetic (T2D or Diabetic mellitus or NIDDM: Non-insulin-dependent diabetic mellitus). That means hyperglycemia+hypertriglyceridemia occur first+insulin resistance, then development of associated diseases such as micro and macrovasculature diseases, kidney failure, heart diseases, etc. Without this specific diet, these animals remain healthy.
Effects of Diet on General Parameters (BW, FI and WI)

The animals gained weight during the course of the study. At the age of 6 week, BW of untreated ZDF rats was of approximately 230 g (Table 2) and reached 410-450 g after 11 weeks of feeding. No significant differences in BW gain were detected between placebo groups fed either a diabetogenic or/and chow diet (high/mid/low) or in comparison to the ZL group. Each animal consumed approximately 30 g per day independent of the type of the diet. No variation in food intake or weight gain was observed during the study in the untreated group_full and group_mild. The group_low showed a slight increase in FI at the time of switch to chow diet.
Effects of Diet on Metabolic Plasma Parameters At the beginning of the study, healthy ZDF rats (6 weeks of age) had relatively normal glucose, $HbA_{1C}$, insulin and TC levels measured under post-prandial conditions (Table 2). In contrast, age-matched ZL rats are characterized by very low insulin and TG levels and elevated NEFA compared to ZDF. These data were in agreement with those reported by the provider (FIG. 2).
Effects of Diet on Glucose Metabolism
Glucose, $HbA_{1c}$ and Insulin Levels ZDF rats continually fed a diabetogenic diet (group_full) became rapidly hyperglycaemic and hyperinsulinemic with elevated $HbA_{1C}$ levels in contrast to the lack of effects in ZL rats on the same diet (FIG. 2). During prolonged maintenance on the diabetogenic diet (ZDF group_full) the rats first rapidly developed hyperinsulinemia and then subsequently became insulin resistant after 4 weeks (i.e. at 10 weeks of age). In ZDF rats fed a diabetogenic diet for 4 w which was then changed to a chow diet (group_mild) showed a similar time course regarding increase in glucose, $HbA_{1C}$ and insulin levels compared to group_full but with a lower extent of hyperglycaemia (23.±1.7 mM vs. 29.5±1.8 mM) (FIG. 4 A).

In ZDF rats fed a diabetogenic diet for 2 week only (group_low), plasma glucose began to rise at the age of 12 weeks (i.e. after 2 weeks of feeding with diabetogenic diet+4 weeks of chow diet), and reached 18.7±2.0 mM at 15 weeks of age of the study which was significantly lower than in both group_full (29.5±1.8 mM) ($p<0.01$) and group_mild (23.9±1.7 mM) (FIG. 4).

Hyperinsulinemia reached after the 2 weeks of feeding with diabetogenic diet (≈6.5 ng/ml) was maintained until 15 weeks of age suggesting absence of beta-cell failure in contrast to group_full and group_mild. At the end of the study group_low exhibits a decrease in insulin levels (FIG. 4C) without changes in glucose levels (17.3±1.9 mM)(FIG. 4A). This functional defect in glucose-stimulated insulin secretion may reflect the progression to insulin deficiency prior to development of a severe diabetic state.

TABLE 2

Basal plasma parameters levels measured in 6W-old ZDF and ZL rats fed with diabetogenic diet.

| Rats | Diet | BW (g) | Glucose (mM) | $HbA_{1C}$ (%) | Insulin (ng/ml) | TG (mM) | NEFA (mM) | TC (mM) |
|---|---|---|---|---|---|---|---|---|
| ZDF | Full | 233 ± 5 | 9.2 ± 0.6* | 4.5 ± 0.1 | 1.9 ± 0.3* | 1.3 ± 0.1** | 0.17 ± 0.04* | 2.9 ± 0.2 |
|  | Mild | 234 ± 5 | 9.5 ± 0.3** | 4.6 ± 0.1 | 2.3 ± 0.4** | 1.6 ± 0.1** | 0.17 ± 0.03* | 3.1 ± 0.1 |
|  | Low | 231 ± 5 | 9.4 ± 0.3** | 4.7 ± 0.1 | 2.3 ± 0.3** | 1.6 ± 0.1** | 0.14 ± 0.02* | 3.1 ± 0.1 |
| ZL | Full | 179 g ± 3 | 7.8 ± 0.1 | 4.8 ± 0.1 | 0.6 ± 0.2 | 0.7 ± 0.0 | 0.42 ± 0.02 | 2.8 ± 0.1 |

*$p < 0.05$ or **$p < 0.01$ compared to ZL rats, ANOVA, followed by Dunnett's post hoc test.

Effects on Postprandial Glucose (OGTT)

Continual feeding of a diabetogenic diet throughout the study (group_full) or for 4 weeks (group_mild) followed by switch to chow diet rendered the rats strongly hyperglycaemic under fasting conditions (elevated FBG) as well as glucose intolerant as revealed by glucose excursion values obtained during an OGTT (FIG. 5). No difference in FBG or glucose excursion (glucose AUC) was noticed between these 2 groups indicating no improvement of glucose tolerance by reducing feeding with diabetogenic diet to 4 weeks. The ZDF rats that continually received a diabetogenic diet (group_full) had severe glucose intolerance compared to ZL (AUC of 2213 vs. 779). The ZDF rats fed a diabetogenic diet for 2 weeks followed by switch chow (group_low) showed only moderate hyperglycaemia under fasting condition (6.9±0.5 mM) compared to the ZDF group_full (9.6±1.0 mM) (Table 3, FIG. 5).

TABLE 3

Effect of dietary conditions on glucose tolerance in ZDF rats. Summary of fasting parameters and glucose excursion (AUC) measured before and during OGTT at the end of the study and feeding period.

| Groups | Diabetogenic Diet | FBG (mM) | Fasting Insulin (ng/ml) | AUC (mM × min) | AUC (delta baseline) |
|---|---|---|---|---|---|
| ZDF | Full | 9.6 ± 1.0** | 1.6 ± 0.2 | 2213 ± 211** | 1066 ± 127** |
|  | Mild | 10.0 ± 1.2** | 1.5 ± 0.3 | 2125 ± 266** | 918 ± 148** |
|  | low | 6.9 ± 0.5* | 3.5 ± 0.8** | 1565 ± 188* | 743 ± 125* |
| ZL | full | 4.3 ± 0.0 | 0.4 ± 0.0 | 779 ± 15 | 269 ± 17 |

N = 8-10 per group
**p < 0.01 or *p < 0.05 compared to ZL rats.
F-test followed by t-test or Mann Whitney.

Nevertheless, the FBG levels of group_low were still significantly higher compared to ZL rats (4.3±0.0 mM. p<0.05). The short feeding period with a diabetogenic diet resulted in substantially elevated fasting insulin levels, strongly reduced fasting glucose levels and elevated insulin resistance index (HOMA) compared to ZL rats (25.4±5.8 vs. 2.0±01, p<0.01) which was maintained over time. This indicated persistent strong insulin resistance in this moderately diabetic rat model.

All together, these data showed that feeding ZDF rats a diabetogenic diet for 4 w or 11 w induced dramatic metabolic changes to a similar extent leading to hyperglycaemia, hypertriglyceridemia, hypercholesterolemia, glucose intolerance and insulin resistance, beta-cell failure. In contrast, restricted access of young ZDF rats to diabetogenic diet for 2 weeks after weaning rendered them modestly diabetic and insulin resistant without signs of beta-cell failure. Feeding ZDF rats a diabetogenic diet for only 2 weeks significantly delayed development of hyperglycaemia. The data shown herein suggested that overall changes in metabolic parameters in group_low were stabilized at 10 weeks of age except for glucose that increase started from 12 weeks of age (FIG. 4).

Effects of Diet on Lipid Metabolism

In addition to hyperglycaemia, elevated $HbA_{1C}$ and beta-cell failure observed in ZDF (group_full), changes in lipid parameters occurred. For example, plasma TG dramatically increased from 1.4±0.1 mM to 10.6±1.8 mM after 4 weeks of feeding a diabetogenic diet. At the end of the study, plasma TG stabilized to 9.59±1.31 mM (FIG. 6). Elevation of plasma TG was accompanied by progressive increase in plasma TC from 2.9±0.2 mM to 4.9±0.3 mM and circulating NEFA (from 0.20±0.04 mM to 0.36±0.02 mM) (FIG. 6). Limiting access to diabetogenic food for the first 4 weeks delayed and transiently reduced severe hypertriglyceridemia (FIG. 6A) that finally did not differ from group_full at the end of the study. In contrast, ZDF rats fed a diabetogenic diet for the first 2 weeks after weaning (group_low) only progressively became hypertriglyceridemic (FIG. 6A). Changes in diet did not lead to differences in the increase in NEFA and TC (FIG. 6 B & C) but significantly increased plasma adiponectin levels after 4 weeks of diet (by 37±7%, 32±6% and 2±11 in group_full, group_mild and group_low, respectively) suggesting a diet-induced insulin resistance effect.

Effects on Islet Morphology and Beta-Cell Integrity

Feeding young ZDF rats a diabetogenic diet during 11 weeks (group_full) induced dramatic changes in beta-cell structure compared to ZL rats fed the same diet. In the pancreas of ZDF rats, disruption of islet architecture is noticed (FIG. 7). Islets are enlarged with irregular projections into the exocrine pancreas, and endocrine cells are scattered within the exocrine tissue. beta-cell death is increased, beta-cell mass is reduced, and the insulin content within beta-cells is reduced (data not showed). (Examination of pancreas of group_low and group_mild is currently under investigation).

Intervention Treatment with Pioglitazone

Metabolic Status of ZDF Rats Before Treatment

Intervention treatment started in 10-weeks-old ZDF and was performed for 7 weeks. At the beginning of the treatment, group_full and group_mild were hyperglycaemic (respectively 17.4±2.6 mM and 13.6±14.0 mM), hyperinsulinemic (4.8±1.0 ng/ml and 7.4±0.5 ng/ml) and had all the lipids parameters increased (especially triglycerides) compared to age matched ZL (FIG. 8 and Figure). Although feeding a diabetogenic diet for only 2 weeks significantly improved plasma parameters levels compared to fully diabetic ZDF (group_full), moderately diabetic ZDF rats (group_low) are still characterized by higher triglycerides, cholesterol and NEFA plasma levels compared to healthy ZL rats (FIG. 6). In contrast, group_low ZDF normoglycemic had values similar to the ZL group (FIG. 4) (6.9±0.5 mM vs. 4.3±0.0 mM, respectively).

Effects of Pioglitazone on BW, FI and WI

Chronic treatment with Pioglitazone increased BW of ZDF rats compared to their respective vehicle group (in agreement with literature data). The increase in BW induced by Pioglitazone was of comparable extent in group_low, group_mild and group_full ZDF rats and was approximately +30% versus vehicle. Moreover, daily food intake (measured over 24 hours) was increased from ≈30 g to ≈50 g in all treated groups. As expected, WI was increased proportionally to changes in FI. Thus, the increase in cumulative FI along the 7 weeks of treatment likely contributed to the increase in BW. Increase in BW by PPAR agonists is a well known effect that is exaggerated in rodents (mice and rats) compared to humans. Despite the increase in body weight under Pioglitazone therapy, the metabolic profile was significantly improved (discussed below).

Effects of Pioglitazone on Glucose Metabolism

Glucose, $HbA_{1C}$ and Insulin Levels

As discussed above, a diabetogenic diet increases plasma glucose, insulin and HbA1c% levels in ZDF rats. Treatment of group_full ZDF rats with Pioglitazone strongly reduced blood glucose levels (FIG. 8A). An improvement in glycaemic control was apparent after 2 weeks of treatment and was partially maintained throughout the duration of treatment. The reduction in circulating glucose was accompanied by a significant reduction of $HbA_{1C}$ (FIG. 8B).

Pioglitazone significantly reduced the hyperinsulinemia of group_full ZDF at the beginning of the treatment, however, this effect was gone after 5 weeks (FIG. 8C). Similarly findings were observed in group_mild ZDF rats suggesting that neither improvement of the diabetic state nor prolonged improvement by therapy was reached in either group_full or group_mild. In contrast, treatment of moderately diabetic ZDF rats (group_low) with Pioglitazone fully prevented the development of hyperglycaemia and the increase in HbA$_{1c}$ to such an extent that both values were similar to those in untreated ZL rats (FIG. 8A,B). Additionally, Pioglitazone strongly reversed hyperinsulinemia starting at week 2 of treatment and this effect was maintained until the end of the study. At the end of the 7 week treatment period, group_low administered Pioglitazone showed significantly reduced insulin levels (2.1±0.2 ng/ml) that were only slightly higher compared to the non-diabetic ZL animals (0.8±0.1 ng/ml, p<0.05).

All together, these data showed that normalization of hyperglycaemia, HbA1c and hyperinsulinemia to levels comparable to ZL rats was achieved in moderately diabetic ZDF rats (group_low) under chronic treatment but not in group_mild or group_full.

Effects of Pioglitazone on Post-Prandial Glucose (OGTT)

ZDF rats on a diabetogenic diet for 11 (group_full) or 4 weeks (group_mild) were extremely glucose intolerant compared to ZDF rats on a diabetogenic diet for only 2 weeks (group_low) which were only moderately glucose intolerant. Nevertheless, glucose excursion measured in group_low after 10 weeks of study was still significantly greater than ZL (AUC: 1565±188 vs. 779±15, see Table 3). Treatment with Pioglitazone for 6 weeks significantly improved glucose tolerance of group_mild and group_full to a similar extent compared to vehicle by 29% and 31%, respectively, although without normalizing it to ZL rats (FIG. 9). In contrast, group_low was a little more sensitive to Pioglitazone treatment since AUC was reduced by 36% compared to vehicle but reached glucose excursion values close to ZL (AUC: 1000±48 and 779±15, respectively).

The strong efficacy of Pioglitazone in improving glucose metabolism in group_low was also reflected in the significant reduction of FBG compared to vehicle (5.1±0.1 mM vs. 6.9±0.4 mM, p<0.05) that also approached the FBG levels in non-diabetic ZL rats (4.3±0.0 mM) (FIG. 9A). In group_mild and group_full, the ability of Pioglitazone to reduce FBG was modest after 7 weeks of treatment since levels reached 6.6±1.3 mM and 6.7±0.9 mM, respectively. These data indicate that pioglitazone is much less effective in animals (group_full and group_mild) in advanced stages of disease.

Effects of Pioglitazone on Lipid Metabolism

Treatment of fully diabetic ZDF rats (group_full) with Pioglitazone strongly reduced plasma triglyceride levels by 69.5±5.2% compared to vehicle. The improvement in TG levels was observed early after the start of treatment (2 weeks) and persisted throughout treatment. However, plasma TG levels remained significantly higher than in ZL rats (2.9±0.6 mM vs. 1.1±0.1 mM, p<0.01) (FIG. 10 A). In addition, a moderate improvement of plasma NEFA levels, paralleling the reduction of plasma TG was observed (data not shown). The effects of Pioglitazone in lowering plasma TG was of a similar magnitude in group_mild and group_full. In contrast, Pioglitazone almost completely and immediately normalized the hypertriglyceridemia of group_low. At the end of treatment, the average plasma TG level of group_low was significantly lower than that of group_full (1.6±0.1 mM vs. 2.8±0.5 mM) reaching a value close to that of the non-diabetic ZL group (1.1±0.1 mM).

Interestingly, Pioglitazone did not change plasma total cholesterol levels in any of the treatment groups (FIG. 10 B). Total cholesterol levels remained elevated in all of the ZDF groups with or without pioglitazone treatment in comparison to the lower levels in the non-diabetic ZL group (2.2±0.1 mM, p<0.01). The absence of TC lowering by Pioglitazone does not mean that there was no change in lipoprotein particles. In fact, Pioglitazone could decrease LDLc and VLDLc, while increasing HDLc without modifying TC levels. FPLC separation and analysis of the lipoprotein composition of the plasma will be required to address this question.

Effect of Pioglitazone on Insulin Resistance

After 6 weeks of treatment, Pioglitazone reduced fasting insulin levels to a comparable level in all groups (full, mild and low: 2.0±0.4, 1.6±0.3 and 1.7+0.1 ng/ml, respectively). HOMA values indicated that group_full was still more insulin-resistant than group-mild or group_low, (14.1±2.7 (full), 10.9±1.9 (mild) and 9.4±0.8 (low)).

Despite significant improvement of metabolic parameters, glucose tolerance and insulin resistance by Pioglitazone in group_low, the HOMA value was still more important than in ZL (2.0±0.1). In all groups, treatment with Pioglitazone increased adiponectin levels by 3-to-5-fold after 7 weeks of treatment and compared to baseline (data not shown) confirming its insulin sensitizing action.

The present invention, thus, relates to a method of producing a diabetic rat comprising feeding rats for 1 to 2 weeks after weaning with a high fat diet. In a preferred embodiment, said rat is a ZDF rat. Said high fat diet is the diabetogenic diet herein described.

A high fat diet is a diet which contains more than 6% fat, preferably more than 1% fat (saturated and/or unsaturated). A Chow diet is a diet which contains less than 6% fat, preferably about 4.5% fat (saturated and/or unsaturated).

Preferably, weaning of the rats occurred after 5 to 6 weeks of age. In a preferred embodiment, said high fat diet comprises Kliba 2437. In a most preferred embodiment, rats are fed for 2 weeks after weaning with said high fat diet.

One important advantage of the rats produced by this method is that diabetes is reversible and that, thus, compounds for interventive therapy can be identified, while with the known models, only compounds for preventive treatment can be identified since the induction of diabetes there is not reversible.

The present invention also provides a method for identifying compounds that can reverse diabetes, comprising the steps of: a) feeding rats for 1 to 2 weeks after weaning with a high-fat diet followed by Chow diet feeding; b) administering a compound of interest; and c) determining whether diabetes is reversed by said compound. Preferably, said rat is a ZDF rat. More preferably, the diabetic rats are the rats produced with the method described hereinbefore. A compound that can reverse diabetes is a compound which, when compared to the effect of a reference compound, or to vehicle alone reverses parameters which are indicative of diabetes to levels comparable to non-diabetic control animals. The reversal of diabetes by said compound, as compared to a negative control, reference of vehicle, can, e.g., be a reduction of blood glucose levels, reduction of HbA$_{1c}$, preferably to a level similar to that of untreated ZL rats; reduction of hyperinsulinemia; reduction of FBG; reduction of AUC; reducing hypertriglyceridemia. For the determination of the reversal of diabetes by a compound, any single one or combination of said parameters, or all of them can be determined, and they may be combined with the measurement of additional parameters. Such additional parameters may include, e.g., examination of the structure of key organs: pancreas (beta-cell), kidneys (glomerulosclerosis) and eyes (cataract, microvascular alteration). Analysis of proteinuria and albuminuria will complete the characterization of this new model of T2D. Additionally, it would also be important to determine the degree of hypertension of this new model since regular ZDF rats are claimed to be mild-hypertensive.

Up to now, no investigations have been reported on pronounced beneficial effects of PPAR gamma or PPAR alpha gamma on animal model gathering features of T2D, insulin resistance and dyslipidemia such as in the ZDF rat model. In previous studies, improvement of the metabolic profile was achieved only during prevention therapy with PPAR alpha gamma agonists (internal data, Shibata et al., 1998) or in ZDF at very early stage of diabetes (8 weeks of age, no insulin resistance, moderate hyperglycaemia) (Pickavance et al., 2005; Brand et al., 2002). For characterizing the present model of moderate T2D, we considered Pioglitazone (Actos®) which is widely used in human beings. In rodent models, efficacy of Pioglitazone was proven at doses ranged between 3-30 mg/kg/d when administered orally. Data generated in obese and insulin resistant Zucker fa/fa rats demonstrated that 10 mg/kg/d were a very efficacious dose (although not maximal).

In the present study, we defined experimental conditions that render adult ZDF rats moderately and stably diabetic and highly sensitive to intervention therapy with an anti-diabetic agent. The present study showed that restricting 5 to 6 weeks-old ZDF rats to a high fat diet for only 4 weeks rendered them as diabetic as ZDF rats maintained continually on a high-fat diet. These highly diabetic animals were poorly sensitive to treatment with Pioglitazone. In contrast, reducing the time on a high fat diet from 4 W to 2 W followed by resumption of a regular chow diet, delayed the onset and the severity of diabetic symptoms (hyperglycaemia, hypertriglyceridemia), prevented overt insulin resistance, prevented beta-cell failure and limited the extent of glucose intolerance. This delayed moderate T2D ZDF model stage was maintained during 11 weeks of study and was much more sensitive to intervention therapy with anti-diabetics.

The data presented herein showed that high fat diet given for 4 weeks irreversibly rendered ZDF fully diabetic but not when fed for 2 weeks. These data suggest that, at some point during the 4 weeks of feeding a diabetogenic diet in ZDF rats, the animals progress into an advanced stage of diabetes, likely accompanied by beta-cell failure that renders them less sensitive to drug therapy. This difference could be due to greater lipotoxicity or glucotoxicity. Without treatment, compensatory hyperinsulinemia was present in group_low but insufficient to normalize hyperglycaemia. Finally, at 17 weeks of age, insulin levels started to decrease maybe reflecting beta-cell failure. Reduced insulin concentration in ZDF rats appears to be caused by defective function of pancreatic beta-cells, associated with decreased insulin content. By the end of the study, as insulin secretion was still high it seemed that 2 weeks of a diabetogenic diet increased insulin content in the islets of ZDF rats at 12 weeks of age. Since 2 weeks of a diabetogenic diet reduced hyperglycemia and delayed triglycerides accumulation, the preservation of beta-cell function observed in group low was in agreement with the consideration that beta-cell failure is a result of an elevated burden on the beta-cells. 1 week of feeding a diabetogenic diet may be sufficient to induce similar metabolic disturbances as in moderately diabetic ZDF rats (group_low).

Since Pioglitazone enhances insulin sensitivity in all groups (treatment with Pioglitazone increased adiponectin levels by 3-to-5-fold) in peripheral tissues (Shibata et al., 1998), it is considered that Pioglitazone suppresses the overworking of beta-cells through improving insulin sensitivity, followed by prevention of hyperglycemia and hyperlipidemia.

In the present study, Pioglitazone prevented hyperglycaemia and hyperlipidemia, but no effect on the level of serum cholesterol has been observed. It has been reported that PPAR alpha regulates lipid metabolism (Brand et al., 2003; Pickavance et al., 2005) and a cholesterol lowering effect on ZDF has been described using a dual PPAR alpha/beta agonist.

Thus, the present invention provides, for the first time, experimental conditions that render adult ZDF rats (1) moderately diabetic in a stable manner and (2) fully sensitive to intervention therapy with anti-diabetics.

REFERENCES

BODEN, G. (2003). Effects of free fatty acids on gluconeogenesis and glycogenolysis. *Life sciences,* 72, 977-88.

BRAND, C., L., STURIS, J., GOTFREDSEN, C., F., FLECKNER, J., FLEDELIUS, C., HANSEN, B., F., ANDERSEN, B., YE, J., MING, SAUERBERG, P. & WASSERMANN, K. (2003). Dual PPARalpha/gamma activation provides enhanced improvement of insulin sensitivity and glycemic control in ZDF rats. In *American journal of physiology. Endocrinology and metabolism.* pp. E841-54. United-States: NLM.

CHEN, D. et al. (2004). Development and applications of rodent models for type 2 diabetes. *Diabetes, Obesity and Metabolism,* 10, 1-13.

GOLDSTEIN, B. J. (2002). Insulin resistance as the core defect in type 2 diabetes mellitus. *American Journal of Cardiology,* 90, 3G-10G.

GREENFIELD, J., R. & CAMPBELL, L., V. (2004). Insulin resistance and obesity. *Clinics in dermatology,* 22, 289-95.

GRIFFIN, M. E., MARCUCCI, M. J., CLINE, G. W., BELL, K., BARUCCI, N., LEE, D., GOODYEAR, L. J., KRAEGEN, E. W., WHITE, M. F. & SHULMAN, G. I. (1999). Free fatty acid-induced insulin resistance is associated with activation of protein kinase C theta and alterations in the insulin signaling cascade. *Diabetes,* 48, 1270-4.

GRUNDY, S., M., BREWER, H., BRYAN, JR, CLEEMAN, J., I., SMITH, S., C, JR, LENFANT, C. & AMERICAN HEART ASSOCIATION, Y. N. H., LUNG, AND BLOOD INSTITUTE. (2004). Definition of metabolic syndrome: Report of the National Heart, Lung, and Blood Institute/American Heart Association conference on scientific issues related to definition. *Circulation,* 109, 433-8.

GURNELL, M., SAVAGE, D., B., CHATTERJEE, V., KRISHNA, K. & O'RAHILLY, S. (2003). The metabolic syndrome: peroxisome proliferator-activated receptor gamma and its therapeutic modulation. *The Journal of clinical endocrinology and metabolism,* 88, 2412-21.

KAHN, B. B. (1998). Type 2 diabetes: when insulin secretion fails to compensate for insulin resistance. *Cell,* 92, 593-596.

KING, H., AUBERT, R. E. & HERMAN, W. H. (1998). Global burden of diabetes, 1995-2025: prevalence, numerical estimates, and projections. *Diabetes care,* 21, 1414-31.

KLEIN, R. (1995). Hyperglycemia and microvascular and macrovascular disease in diabetes. *Diabetes care,* 18, 258-68.

RANDLE, P. J., GARLAND, P. B., HALES, C. N. & NEWSHOLME, E. A. (1963). The glucose fatty-acid cycle Its role in insulin sensitivity and the metabolic disturbances of diabetes mellitus. *Lancet,* 1, 785-9.

MATSUZAWA, Y., FUNAHASHI, T. & NAKAMURA, T. (1999). Molecular mechanism of metabolic syndrome X: contribution of adipocytokines adipocyte-derived bioactive substances. *Annals of the New York Academy of Sciences,* 892, 146-54.

MURRAY, R. K et al. (2000). *Harper's biochemistry*, Appleton & Lange.

PICKAVANCE, L., C., BRAND, C., L., WASSERMANN, K. & WILDING, J., P. H. (2005). The dual PPARalpha/gamma agonist, ragaglitazar, improves insulin sensitivity and metabolic profile equally with pioglitazone in diabetic and dietary obese ZDF rats. *British journal of pharmacology*, 144, 308-16.

POSPISILIK, J., A., STAFFORD, S., G., DEMUTH, H., ULRICH, MCINTOSH, C., H. S. & PEDERSON, R., A. (2002a). Long-term treatment with dipeptidyl peptidase IV inhibitor improves hepatic and peripheral insulin sensitivity in the VDF Zucker rat: a euglycemic-hyperinsulinemic clamp study. *Diabetes*, 51, 2677-83.

POSPISILIK, J. A., STAFFORD, S. G., DEMUTH, H. U., BROWNSEY, R., PARKHOUSE, W., FINEGOOD, D., T., MCINTOSH, C. H. S. & PEDERSON, R. A. (2002b). Long-term treatment with the dipeptidyl peptidase IV inhibitor P32/98 causes sustained improvements in glucose tolerance, insulin sensitivity, hyperinsulinemia, and beta-cell glucose responsiveness in VDF fa/fa Zucker rats. *Diabetes*, 51, 943-50.

REAVEN, G. M. (1988). Banting lecture 1988 Role of insulin resistance in human disease. *Diabetes*, 37, 1595-607.

RUBIN, R. J., ALTMAN, W. M. & MENDELSON, D. N. (1994). Health care expenditures for people with diabetes mellitus, 1992. *The Journal of clinical endocrinology and metabolism*, 78, 809A-809F.

SCHERRER, U. & SARTORI, C. (1997). Insulin as a vascular and sympathoexcitatory hormone: implications for blood pressure regulation, insulin sensitivity, and cardiovascular morbidity. *Circulation*, 96, 4104-13.

SCHNEIDER, S. H. & MORGADO, A. (1995). Effects of fitness and physical training on carbohydrate metabolism and associated cardiovascular risk factors in patients with diabetes. *Diabetes Reviews*, 3, 378-407.

SHIBATA, T., TAKEUCHI, S., YOKOTA, S., KAKIMOTO, K., YONEMORI, F. & WAKITANI, K. (2000). Effects of peroxisome proliferator-activated receptor-alpha and -gamma agonist, JTT-501, on diabetic complications in Zucker diabetic fatty rats. *British journal of pharmacology*, 130, 495-504.

STIEGLER, H., STANDL, E., SCHULZ, K., ROTH, R. & LEHMACHER, W. (1992). Morbidity, mortality, and albuminuria in type 2 diabetic patients: a three-year prospective study of a random cohort in general practice. *Diabetic medicine*, 9, 646-53.

TEUTSCH, S., NEWMAN, J. & EGGERS, P. (1989). The problem of diabetic renal failure in the United States: an overview. *American journal of kidney diseases*, 13, 11-3.

TINKER, L. F., HEINS, J. M. & HOLLER, H. J. (1994). Commentary and translation: 1994 nutrition recommendations for diabetes Diabetes Care and Education, a Practice Group of the American Dietetic Association. *Journal of the American Dietetic Association*, 94, 507-11.

UKPDS. (1998). Intensive blood-glucose control with sulphonylureas or insulin compared with conventional treatment and risk of complications in patients with type 2 diabetes UKPDS 33 UK Prospective Diabetes Study UKPDS Group. *Lancet*, 352, 837-53.

| List of abbreviations | |
|---|---|
| AUC | Area under the curve |
| BRdU | bromodeoxyuridin |
| BW | Body weight |
| FBG | Fasting blood glucose |
| FPLC | Fast performance liquid chromatography |
| HbA$_{1c}$ | Glycosylated Hemoglobin A1 |
| HDLc | High density lipoprotein cholesterol |
| HGP | Hepatic glucose production |
| HOMA | Insulin resistance index |
| LDLc | Low density lipoprotein cholesterol |
| NEFA | Non-esterified fatty acids |
| NFE | Nitrogen free extract (extract after removal of moisture, protein, fat, fiber and minerals (ash)) |
| OGTT | Oral glucose tolerance test |
| PAS | Periodic Acid Schiff reagent |
| PPAR | Peroxisome proliferators-activated receptor |
| SEM | Standard error of the mean |
| T2D | Type 2 diabetes |
| TC | Total cholesterol |
| TG | Triglycerides |
| VLDLc | Very low density lipoprotein cholesterol |
| WAT | White adipose Tissue |
| WI | Water intake |
| ZDF | Zucker Diabetic Fatty rats |
| ZL | Zucker Lean rats |

EXAMPLES

Example 1

Animals

In this study 5 week-old, non-diabetic, male ZDF rats (ZDF fa/fa or ZDF) and lean littermates (aged-matched) rats (ZDF+/? or ZL) were purchased from Ch. River Laboratories. The animals were housed by 3 or 4 per cage in a room with 22 to 24° C. temperature, 50% to 60% of humidity with a 12:12 day-night cycle (light from 6:00 AM to 6:00 PM). Rats were fed ad libitum and had permanent access to water. Fresh food was provided weekly, the water was changed twice a week and cages were cleaned 3 times a week.

Male ZDF rats homozygous for non-functional leptin receptors (fa/fa) develop obesity, hyperlipidemia and hyperglycaemia. In contrast, rats with homozygous dominant ((Þ/Þ)) and heterozygous (fa/Þ) genotypes remain lean, normoglycaemic and non-diabetic (Table 1).

Figure 3:
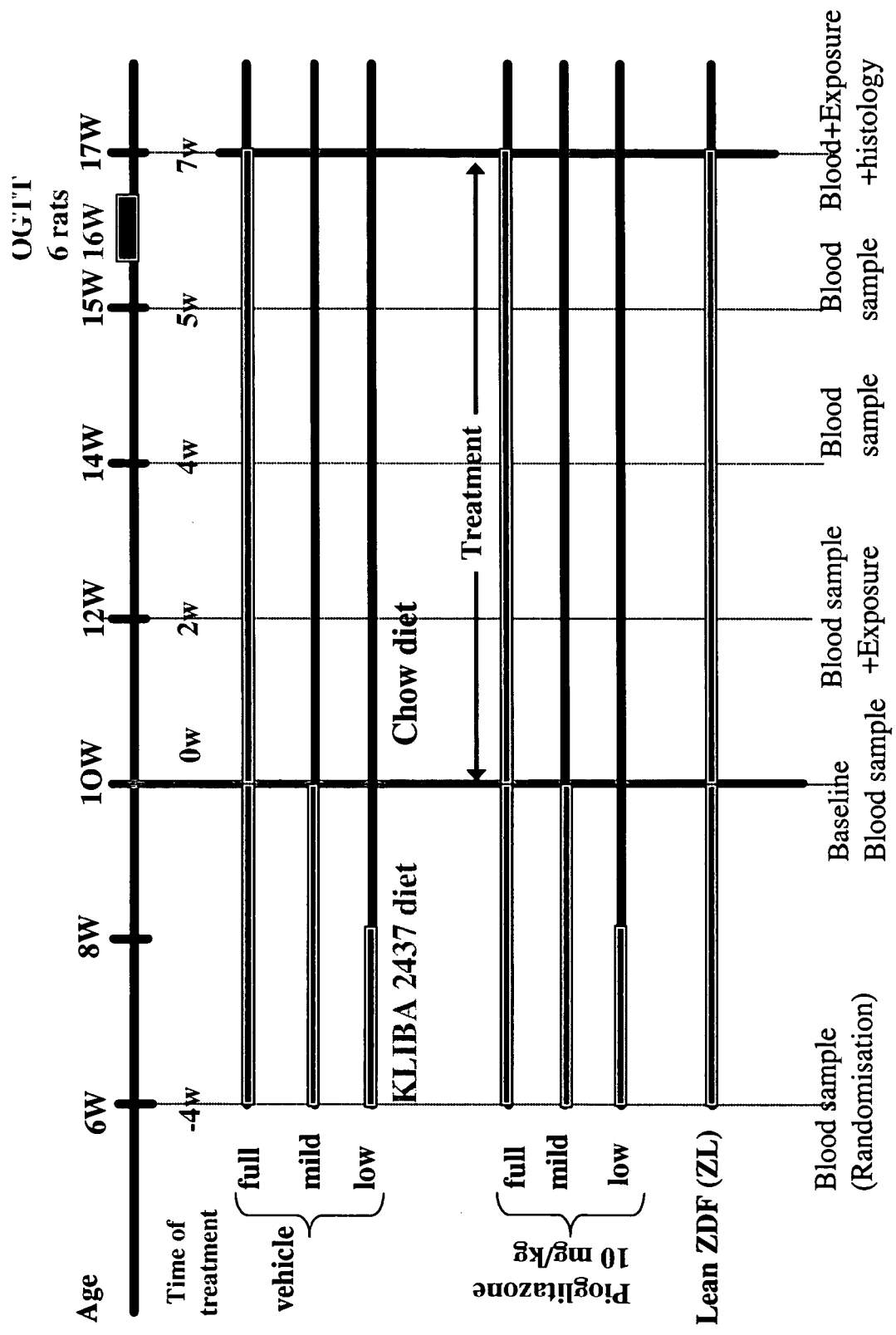

ZDF and ZL rats were ordered at the age of 5 W. After arrival and following 1 week of adaptation, 1 ml of blood was collected retro-orbitally after a short narcosis (isoflurane) in 6 W-old rats. According to glucose, insulin, triglycerides, NEFA, cholesterol plasma levels and the BW, rats are randomized in 6 groups of 10 ZDF fatty rats. A group of 10 ZL rats was formed and followed as a control group along the study duration (FIG. 3). Three groups of ZDF rats receive either vehicle (untreated) or Pioglitazone (treated) as food Admix. In each untreated/treated group of ZDF rats, one is fed a high fat diet during 11 weeks (group_full), during 4 weeks (group_mild) or during 2 weeks (group_low).

Example 2

Food and Treatment Preparation

Treatment was administered orally and prepared as food-admix. This mode of administration was preferred over oral gavage to reduce stress to the animals, avoid dosing errors and minimize handling. Pioglitazone (sufficient for 90 kg food)

was dissolved in 18 liters of water. For the three treatment groups of 10 rats each, 6 liters of solution was combined with 30 kg of the diabetogenic diet (KLIBA 2437 with 7% of fat) or 12 liters were mixed with 60 Kg of the chow diet (Kliba 3436). The food was carefully dried at a temperature not exceeding 40° C. and then pelleted. Assuming an average food consumption of approximately 100 g per kg of body weight per day, each animal would be expected to receive a dose of pioglitazone of 10 mg per kg body weight per day. The graphs and tables present the data according to expected daily dose. Daily food intake was recorded during the study and confirmed that each rat consumed on average 100 g food/kg BW per day (data not shown).

The following detailed protocol was used as a non-limiting example:

A group of 60 ZDF/GMI-fa/fa and a group of 10 ZDF/GMI-+/? Lean rats (GMI/Charles River) of 5 weeks of age were fed with high carbohydrate diet (KLIBA 2437, 35% starch, 5% sucrose). The lean ZDF group of rats is kept as control.

5 days after adaptation period, at 9 h A.M., 1 ml of blood was collected retro-orbital after a short narcose with Isoflurane. According to the glucose, insulin, triglycerides, NEFA, cholesterol plasma levels and the Body Weight, the rats were randomized in 6 groups of 10 ZDF fatty rats and 1 group of 10 ZDF lean rats. Three groups out of 6 were treated with vehicle and 3 with pioglitazone. One group of each was fed with high fat diet during 12 weeks, 4 weeks or 2 weeks. 4 rats from the same slot were used for baseline histopathological measurements.

The groups 1 received ZDF KLIBA MIX1 Vehicle Buffer in the diet 2437 ad libitum. The groups 2 and 3 received ZDF KLIBA MIX2 Vehicle Buffer in the diet 3430 ad libitum. The groups 4 received ZDF KLIBA MIX3 (Pioglitazone 10 mg/kg diet 2437) ad libitum. The groups 5 and 6 received ZDF KLIBA MIX4 (Pioglitazone 10 mg/kg diet 3430) ad libitum. The groups 7 (lean) received ZDF KLIBA MIX1 Vehicle Buffer in the diet 2437 ad libitum.

Every two weeks, 1 ml of blood was collected retroorbital after a short narcose with Isoflurane for different blood and plasma parameters. At the beginning, in the middle and at the end of the treatment urinary parameters were collected by using strips for urinalysis (Labstix from bayer).

After 7 weeks of treatment an OGTT was performed on 6 fasted rats. A week later, 2.5 ml of blood was collected retro-orbital after a short narcose with Isoflurane in fed conditions in all animals. Finally, 7 rats per group were sacrificed after the last blood collection and the liver is removed and weighted. 1 week later the last 3 rats per group (from the OGTT group) were given to E. Atzpodien for histological and immunohistological examinations.

Formulation:

Dispersion of the compounds (9 g) in 18 l of aqueous vehicle.

Mix of 6 L solutions in 30 kg pulverized food 2437 and palatability of the food by KLIBA.

Mix of 12 L solutions in 60 kg pulverized food 3430 and palatability of the food by KLIBA Food:

ZDF Diet (Kliba 2437±compounds) during 12 w, 4 w, or 2 w.

ZDF stabilization diet (Kliba 3430±compounds)

Diet composition (Kliba 2437 & Kliba 3436)

| Special diet for ZDF Rats 2437 | | |
|---|---|---|
| Ingredients | | |
| Maize, Soy bean extraction meal, Wheat, herring meal, wheat bran, Pork fat, Wheat starch, | | |
| Molasses, brewer's yeast, whear germ, oat, sugar beet chips, | | |
| grass meal, poultry meat meal, | | |
| Whey powder | | |
| Salt, Calcium carbonate, Dicalcium phosphate, Magnesium oxide | | |
| Trace elements premixes, Vitamin premixes | | |
| | | [approx. Energy %] |
| Dry content | 88.0% | |
| Crude protein | 23.5% | [27.3] |
| Crude fibers | 3.7% | |
| Crude fat | 6.6% | [17.0] |
| Ash | 6.3% | |
| NFE | 47.9% | [55.7] |
| digestible Energy | 14.37 MJ/kg | |
| Starch | 34.90% | |
| Sugar | 4.46% | |
| Amino acids | | |
| Arginine | | 1.44% |
| Lysine | | 1.41% |
| Methionine | | 0.44% |
| Methionine + Cystine | | 0.81% |
| Tryptophane | | 0.27% |
| Threonine | | 0.90% |
| Minerals | | |
| Calcium | | 1.00% |
| Phosphorus | | 0.65% |
| Sodium | | 0.29% |
| Potassium | | 0.93% |
| Magnesium | | 0.20% |
| Chloride | | 0.49% |
| Trace elements | | |
| Copper | | 15 mg/kg |
| Zinc | | 75 mg/kg |
| Iron | | 230 mg/kg |
| Iodide | | 1.2 mg/kg |
| Manganese | | 60 mg/kg |
| Selenium | | 0.35 mg/kg |
| Vitamins | | addition/kg Food |
| Vitamin A | | 15'000 IE |
| Vitamin D3 | | 3'300 IE |
| Vitamin E | | 89 mg |
| Vitamin K3 | | 4 mg |
| Vitamin B1 | | 16 mg |
| Riboflavine | | 8 mg |
| Nicotinic acid | | 60 mg |
| Pantothenic acid | | 25 mg |
| Folic acid | | 3 mg |
| Vitamin B6 | | 7 mg |
| Vitamin B12 | | 0.03 mg |
| Biotin | | 0.2 mg |
| Choline | | 1093 mg |
| Vitamin C | | 30 mg |

| SMALL RODENTS ALL PUPOSE DIET, EXTRUDATE 3436 | |
|---|---|
| Ingredients | |
| Cereal products and products rich in energy: | |
| Barley, wheat, wheat bran, wheat starch, maize, soya bean oil Sources of vegetable protein: | |
| Soya bean extraction meal (NGVO), brewer's dried yeast Sources of animal protein: | |
| Poultry meat meal, dried whey powder Sources of minerals: | |
| Di-calcium phosphate, calcium carbonate, salt Amino acids: | |
| L-lysine, DL-methionine Vitamin premixes - trace element premixes | |
| Major nutrients | |
| Dry matter | 88.0% |
| Crude protein | 18.5% |
| Crude fibre | 4.5% |
| Crude fat | 4.5% |
| Ash | 6.3% |
| NFE | 54.2% |
| ME mouse/rat | 12.5 MJ/kg |
| Starch | 35% |
| Amino acids | |
| Arginine | 1.10% |
| Lysine | 1.00% |
| Methionine | 0.39% |
| Methionine + cystine | 0.75% |
| Tryptophan | 0.20% |
| Threonine | 0.65% |
| Macrominerals | |
| Calcium | 1.05% |
| Phosphorus | 0.80% |
| Available phosphorus | 0.38% |
| Sodium | 0.20% |
| Potassium | 0.78% |
| Magnesium | 0.20% |
| Chlorine | 0.36% |
| Trace elements | |
| Copper | 14 mg/kg |
| Zinc | 60 mg/kg |
| Iron | 250 mg/kg |
| Iodine | 1 mg/kg |
| Manganese | 60 mg/kg |
| Selenium | 0.3 mg/kg |

| Vitamins | Addition/kg | content total/kg after extrusion (approx.) |
|---|---|---|
| Vitamin A | 18'000 IE | 14'000 IE |
| Vitamin D3 | 1'000 IE | 1'000 IE |
| Vitamin E | 100 mg | 110 mg |
| Vitamin K3 | 7 mg | 0.05-2 mg |
| Vitamin B1 | 30 mg | 30 mg |
| Vitamin B2 | 20 mg | 20 mg |
| Nicotinic acid | 40 mg | 60-70 mg |
| Pantothenic acid | 33 mg | 33 mg |
| Folic acid | 2 mg | 2.2 mg |
| Vitamin B6 | 14 mg | 14 mg |
| Vitamin B12 | 0.05 mg | 0.05 mg |
| Biotin | 0.2 mg | 0.22 mg |
| Choline | 1'000 mg | 2'000 mg |
| Vitamin C | 40 mg | — |

| SMALL RODENTS ALL PUPOSE DIET, EXTRUDATE 3436 | | |
|---|---|---|
| Delivery form: | 3436.0.13: | Extrudate 15 mm in 12.5 kg paperbags |
| | 3436.0.12: | Extrudate 15 mm in 12.5 kg paperbags with sealed polyethylene inlays |

Given values are calculated averages in air-dry feed ingredients

Example 3

Chemical Products

Pioglitazone [(±)-5-[[4-[2-(5-ethyl-2-pyridinyl)ethoxy]phenyl]methyl]-2,4-] has a molecular formula of $C_{19}H_{20}N_2O_3S \cdot HCl$ and a molecular weight of 392.90 Daltons. The structural formula is as shown:

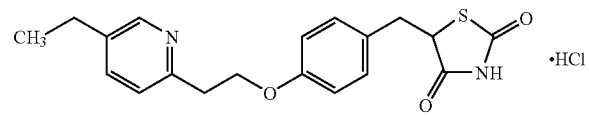

Pioglitazone was provided by Sequoia, U.K. and is registered under the name Actos®

Example 4

Blood and Organs Collection and Biochemical Analyses

Blood sampling was always performed in the morning (9-11 am) 2-to-5 hours after feeding session and 2 h after last oral dosing (food was removed at 7:00 am). Blood (≈200 μl) was harvested retro-orbitally from slightly anesthetized rats (isoflurane) into tubes containing EDTA and kept on ice bed until centrifugation (6000 RPM for 20 minutes at 4° C.). The time course of blood sampling began at 6 weeks of age, at baseline (10 W) and after 2 W, 4 W, 5 W and 7 W of treatment (i.e. at 12 W, 14 W, 15 W and 17 W, respectively).

Main plasma biochemical parameters (glucose(Glucoquant, e.g. Ref. 1447513), TG (eg. 11730711), TC (CHOL (eg. 11491458)), NEFA (Cat No. 11 383 175 001); all from Roche Molecular Diagnostics) were quantified using fluorometric methods. Quantification of $HbA_{1c}$ (%) was performed in whole blood, using an immuno-turbidimetric assay (Tinaquant, e.g. 11822039 from Roche Molecular Diagnostics). Glycosylated haemoglobin ($HbA_{1c}$) is formed by the non-enzymatic covalent attachment of glucose to normal haemoglobin (HbA). In erythrocytes the rate of HbA converted into $HbA_{1c}$ is increasing with the mean rate of blood glucose. Since $HbA_{1c}$ is stable for about 10 weeks in erythrocytes, its level reflects the glycaemic balance during the past few weeks before measurement. $HbA_{1c}$ is a predictor of diabetic complications and interventions that reduce $HbA_{1c}$ correspondingly reduce the risk of complications (UKPDS, 1998). $HbA_{1c}$ (%) was calculated as presented: $HbA_{1c}$ %=87.6*(HBA1c/Hb)+2.27.

Commercially available ELISA kits (LINCO®) were used to quantify plasma concentration of insulin and adiponectin. Adiponectin is an adipokine which is negatively correlated with insulin sensitivity and fasting plasma insulin concentration (Goldstein, 2002). Adiponectin plasma concentrations are decreased in T2D patients and despite the fact that it is produced by adipocytes, as an individual becomes more obese, the adiponectine is decreased and insulin resistance increases (Matsuzawa et al., 1999).

Oral Glucose Tolerance Tests (OGTTs) were performed in 6 of the 10 animals in each group. After 6 weeks of treatment (16 W of age), rats were fasted overnight (≈16 h). Blood was then collected in conscious animals (tail vein) for baseline glucose and insulin measurements. The animals were then orally administered glucose (1 g/kg BW) and the time course of plasma glucose was determined at +15', +30', +60' and +120' by direct blood glucose concentration determination (by GlucoTrend®). Studying the evolution of blood glucose concentration along time after a load of glucose will give information about the ability of the organism to use glucose. Using the trapezoidal rule, glucose tolerance was calculated as area under the curve (AUC) of glucose concentration during 120 min and the change from baseline was calculated (delta AUC). HOMA index is also assessed during the OGTT by considering fasting insulin and fasting blood glucose (FBG) levels. HOMA: [FBG (mM)*(Fasting Insulin (µU))/22.5]. HOMA-index translates peripheral insulin resistance. Measurement of insulin was performed using Mercodia Rat Insulin ELISA kit.

At the conclusion of the study, the rats were sacrificed by decapitation (after slight narcosis), blood was collected from all animals and organs were harvested from 3 animals per group (pancreas, liver, kidneys, WAT, eyes) for histological and immunohistological examinations.

Example 6

Body Weight/Food Intake Measurements

Body weight and food consumption were recorded with an on-line data acquisition system (DATATOX) using electronic balances.

Example 7

Histopathologic and Immunohistochemical Analysis

At the end of the 7 weeks treatment period, all animals were sacrificed with $CO_2$, exsanguinated and submitted to necropsy. Six hours before necropsy, 3 rats/group were injected intraperitoneally with 100 mg/kg BrdU (bromodeoxyuridine, which is a common chemical used in the detection of proliferating (alive) cells in living tissues). Liver, kidneys, pancreas, and mesenteric white adipose tissue (WAT) were sampled and fixed in 10% buffered formalin for at least 24 hours. In addition, pieces of the kidneys and pancreas were fixed in 2% formaldehyde and 2.5% glutaraldehyde with 2 mg/ml $CaCl_2$ in 0.1 M Na-Cacodylate buffer (pH 7.4) for transmission electron microscopy. After fixation, all organs were embedded in Paraplast. Sections were cut at 2-3 µm and stained as follows: Hematoxylin eosin (HE): liver, kidneys, pancreas, WAT; PAS: kidneys; Fat Red: frozen kidney sections. Slides containing pancreas sections were stained for immunohistochemical evaluation with antibodies to detect BrdU, -insulin, -glucagon, -somatostatin, or both BrdU and insulin.

Example 8

Data Collection and Analysis

All raw data (general parameters (BW, FI) and blood and plasma parameters) were collected manually or on excel tables, then put in electronic form into formatted excel sheets and stored on secured Roche server that included a daily back-up. Values were analyzed as mean±SEM.

Data are expressed as mean±SEM. Parameters were compared between diabetic (ZDF) and Lean controls by unpaired t-test or Mann-Whitney test for non-normally distributed data. The diet effect on each of the parameters was measured by comparing values in each of the different diet group with those in the group-full by one-way ANOVA followed by Dunett's test for multiple comparisons with a control. Significance of difference between each treated group and their respective control untreated group was evaluated by t-test or Mann-Whitney test (an F-test is previously performed to test for variance homogeneity).

Data Analysis was done using the software STATVIEW for Windows (Version 5.01, SAS institute Inc., SAS Campus Drive, Cary, N.C. 27513).

The invention claimed is:

1. A method of producing a diabetic rat comprising feeding male Zucker Diabetic Fatty (ZDF) rats for 1 to 2 weeks after weaning with a high fat diet feed having a fat content of greater than 6% followed by maintenance feeding with a lower fat diet feed having a fat content of up to 4.5%, wherein the diabetes is reversible.

2. The method of claim 1, wherein weaning occurs after 5 to 6 weeks.

3. The method of claim 1, wherein said high fat diet feed has a fat content of about 6.5% and said lower fat diet feed has a fat content of 4.5%.

4. A method for identifying compounds that can reverse diabetes, comprising the steps of
   a) feeding male Zucker Diabetic Fatty (ZDF) rats for 1 to 2 weeks after weaning with a high fat diet followed by a lower fat diet, having a fat content of up to 4.5%, feeding
   b) administering a compound of interest, and
   c) determining whether diabetes is reversed by said compound.

* * * * *